(12) United States Patent
Elia et al.

(10) Patent No.: US 11,576,844 B2
(45) Date of Patent: Feb. 14, 2023

(54) SYSTEMS AND METHODS FOR ASSESSMENT OF LUNG TRANSPULMONARY PRESSURE

(71) Applicant: ART Medical Ltd., Netanya (IL)

(72) Inventors: Liron Elia, Kiryat-Ata (IL); Gavriel J. Iddan, Haifa (IL)

(73) Assignee: ART MEDICAL Ltd., Netanya (IL)

( * ) Notice: Subject to any disclaimer, the term of this patent is extended or adjusted under 35 U.S.C. 154(b) by 0 days.

(21) Appl. No.: 16/638,765

(22) PCT Filed: Apr. 24, 2018

(86) PCT No.: PCT/IL2018/050449
§ 371 (c)(1),
(2) Date: Feb. 13, 2020

(87) PCT Pub. No.: WO2019/035114
PCT Pub. Date: Feb. 21, 2019

(65) Prior Publication Data
US 2021/0128413 A1   May 6, 2021

Related U.S. Application Data

(60) Provisional application No. 62/545,501, filed on Aug. 15, 2017.

(51) Int. Cl.
*A61J 15/00* (2006.01)
*G16H 20/40* (2018.01)
(Continued)

(52) U.S. Cl.
CPC .......... *A61J 15/0084* (2015.05); *A61B 5/037* (2013.01); *A61B 5/085* (2013.01); *A61B 5/6853* (2013.01);
(Continued)

(58) Field of Classification Search
None
See application file for complete search history.

(56) References Cited

U.S. PATENT DOCUMENTS

| | | | |
|---|---|---|---|
| 9,554,740 B2* | 1/2017 | Saeed | G16H 10/60 |
| 2005/0124908 A1* | 6/2005 | Belalcazar | A61B 5/0537 |
| | | | 600/547 |

(Continued)

FOREIGN PATENT DOCUMENTS

| | | |
|---|---|---|
| EP | 1892010 | 2/2008 |
| WO | WO 2016/046707 | 3/2016 |
| WO | WO 2019/035114 | 2/2019 |

OTHER PUBLICATIONS

Ballantine, T. V., et al. "The work of breathing: potential for clinical application and the results of studies performed on 100 normal males." Annals of surgery 171.4 (1970): 590. (Year: 1970).*

(Continued)

*Primary Examiner* — Jacqueline Cheng
*Assistant Examiner* — Jairo H Portillo

(57) ABSTRACT

There is provided a system for monitoring transpulmonary pressure of a mechanically ventilated individual, comprising: a feeding tube, at least one esophageal body, a pressure sensor, and a memory having stored thereon code for: computing an estimate of esophageal wall pressure according to pressure in the esophageal body when inflated and contacting the inner wall of the esophagus, computing the transpulmonary pressure of the mechanically ventilated target individual according to the esophageal wall pressure, periodically inflating and deflating the esophageal body for periodic monitoring of the transpulmonary pressure of the mechanically ventilated target patient while the feeding tube is in use, and computing instructions for adjustment of parameter(s) of a mechanical ventilator that automatically ventilates the target individual according to the computed (Continued)

transpulmonary pressure, wherein the instructions for adjustment of parameter(s) of the mechanical ventilator are computed while the feeding tube is in place without removal of the feeding tube.

22 Claims, 14 Drawing Sheets

(51) Int. Cl.
    *G16H 50/30*     (2018.01)
    *G16H 40/63*     (2018.01)
    *A61B 5/03*     (2006.01)
    *A61B 5/085*     (2006.01)
    *A61B 5/00*     (2006.01)

(52) U.S. Cl.
    CPC .......... *A61B 5/7275* (2013.01); *A61B 5/7282* (2013.01); *A61B 5/746* (2013.01); *A61B 5/7435* (2013.01); *A61J 15/0003* (2013.01); *A61J 15/0049* (2013.01); *G16H 20/40* (2018.01); *G16H 40/63* (2018.01); *G16H 50/30* (2018.01); *A61J 2200/70* (2013.01)

(56) References Cited

U.S. PATENT DOCUMENTS

| | | | | |
|---|---|---|---|---|
| 2009/0118626 | A1* | 5/2009 | Moon | A61B 5/0809 |
| | | | | 600/484 |
| 2010/0274225 | A1* | 10/2010 | Nishtala | A61B 5/6852 |
| | | | | 604/514 |
| 2012/0215081 | A1* | 8/2012 | Euliano | A61B 5/037 |
| | | | | 600/323 |
| 2012/0302922 | A1* | 11/2012 | Chuang | A61B 5/0053 |
| | | | | 600/587 |
| 2014/0155965 | A1* | 6/2014 | Kulstad | A61F 7/12 |
| | | | | 607/105 |
| 2015/0173634 | A1 | 6/2015 | Pintel | |
| 2015/0217069 | A1 | 8/2015 | Novotni et al. | |
| 2016/0151248 | A1 | 6/2016 | Elia et al. | |
| 2016/0256076 | A1* | 9/2016 | Kassab | A61B 5/1076 |
| 2017/0143248 | A1* | 5/2017 | Mabary | A61B 5/6885 |
| 2017/0304154 | A1* | 10/2017 | Azzolini | A61J 15/0076 |
| 2018/0304046 | A1* | 10/2018 | Griffith | A61J 15/0065 |

OTHER PUBLICATIONS

International Preliminary Report on Patentability dated Feb. 27, 2020 From the International Bureau of WIPO Re. Application No. PCT/IL2018/050449. (10 Pages).

International Search Report and the Written Opinion dated Sep. 12, 2018 From the International Searching Authority Re. Application No. PCT/IL2018/050449.

Arnal "Transpulmonary Pressure Measurement", Hamilton Mediical, Retrieved from Internet, 5P., Feb. 8, 2022.

Draeger "Esophageal and Transpulmonary Pressure Literature List 2020", Draeger, 7P., Retrieved from Internet, Feb. 8, 2022.

Seda "[NutriVent] Esophageal Pressure Monitoring", Seda, 17.P., Retrieved from Internet, Feb. 8, 2022.

\* cited by examiner

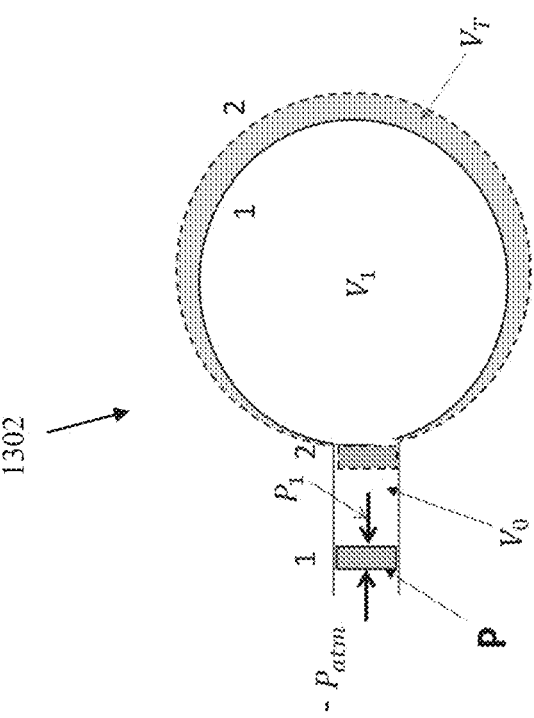

1304

Initial lung volume $V_1$
Final lung volume $V_2$
Tidal volume    $V_T = V_2 - V_1$
Ventilator displacement volume $V_0$
Initial pressure $P_1$    Final pressure $P_2$
                          Pressure increase $\Delta P$
By generalized Young modulus:
$$\Delta P = k V_T$$
By Boyle's law (PV=Const.) for isothermal processes:
$$(V_1 + V_0)P_1 = (V_1 + V_T)(P_1 + \Delta P)$$
Combining the two equations with some algebra we get:
$$V_T = \frac{1}{1 + k\frac{V_1}{P_1}} V_0 = \frac{P_1 V_0}{P_1 + k V_1}$$

1302 schematic description of the ventilation inspiration

FIG. 13

SYSTEMS AND METHODS FOR ASSESSMENT OF LUNG TRANSPULMONARY PRESSURE

RELATED APPLICATIONS APPLICATION

This application is a National Phase of PCT Patent Application No. PCT/IL2018/050449 having International filing date of Apr. 24, 2018, which claims the benefit of priority under 35 USC § 119(e) of U.S. Provisional Patent Application No. 62/545,501 filed on Aug. 15, 2017. The contents of the above applications are all incorporated by reference as if fully set forth herein in their entirety.

BACKGROUND

The present invention, in some embodiments thereof, relates to intra-body measurements and, more specifically, but not exclusively, to systems and methods for measurement of lung transpulmonary pressure.

The ventilation pressure delivered to ventilated patients (e.g., in the ICU) is selected to be sufficient to provide oxygen to the patient without causing damage to the lung of the patient. The ventilation pressure should be set to achieve a desired level of oxygen saturation while maintaining a minimal stress on the lungs which may be subjected to ARDS. Low pressure level or low air volume exchange in the lungs will mean insufficient oxygenation while excess pressure may be damaging to the alveoli and cause other negative effects.

SUMMARY

According to a first aspect, a system for monitoring a transpulmonary pressure of a mechanically ventilated target individual, the system comprises: a feeding tube for insertion into a distal end of an esophagus of the mechanically ventilated target patient, at least one esophageal body having a pressure dependent volume, coupled to a distal portion of the feeding tube, a pressure sensor that senses the pressure in the at least one esophageal body, and a non-transitory memory having stored thereon a code for execution by at least one hardware processor of a computing device, the code comprising code for: computing an estimate of esophageal wall pressure of the esophagus according to the pressure in the at least one esophageal body when the at least one esophageal body is inflated and is contacting the inner wall of the esophagus, computing the transpulmonary pressure of the mechanically ventilated target individual according to the esophageal wall pressure, periodically inflating and deflating the at least one esophageal body for periodic monitoring of the transpulmonary pressure of the mechanically ventilated target patient while the feeding tube is in use, and computing instructions for adjustment of at least one parameter of a mechanical ventilator that automatically mechanically ventilates the target individual according to the computed transpulmonary pressure, wherein the instructions for adjustment of at least one parameter of the mechanical ventilator are computed while the feeding tube is in place without removal of the feeding tube.

According to a second aspect, method of monitoring a transpulmonary pressure of a mechanically ventilated target individual, the system comprises: providing a feeding tube for insertion into a distal end of an esophagus of the mechanically ventilated target patient, wherein at least one esophageal body having a pressure dependent volume is coupled to a distal portion of the feeding tube, computing an estimate of esophageal wall pressure of the esophagus according to the pressure in the at least one esophageal body when the at least one esophageal body is inflated and is contacting the inner wall of the esophagus, computing the transpulmonary pressure of the mechanically ventilated target individual according to the esophageal wall pressure, periodically inflating and deflating the at least one esophageal body for periodic monitoring of the transpulmonary pressure of the mechanically ventilated target patient while the feeding tube is in use, and computing instructions for adjustment of at least one parameter of a mechanical ventilator that automatically mechanically ventilates the target individual according to the computed transpulmonary pressure, wherein the instructions for adjustment of at least one parameter of the mechanical ventilator are computed while the feeding tube is in place without removal of the feeding tube.

At least some implementations of the systems, methods, apparatus, and/or code instructions described herein relate to the technical problem of preventing the development of acute respiratory distress syndrome (ARDS) and/or treating ARDS in a target individual based on monitoring of transpulmonary pressure of the target individual. In particular, continuously (or near continuously, for example, at closely spaced intervals, for example, every minute, 5 minutes, or 10 minutes) monitoring the transpulmonary pressure. The transpulmonary pressure is measured in order to assess the correct amount of ventilation pressure to provide to a ventilated patient in order to ensure that the alveoli of the lungs receive sufficient oxygen without causing damage to the lungs. For example, the lungs in patients with ARDS do not function properly, and therefore require additional ventilation pressure for properly oxygenation. The improper functioning of the lung may occur for other reasons than ARDS, For example, in some patients abdominal organs may press against the diaphragm and the lungs cavity, thus resisting the respiration and hence reducing the blood oxygenation by the alveoli, even though the mechanical ventilation machine displays a sufficient airway pressure. The common medical practice for treatment of patients with abnormally functioning lungs (e.g., due to ARDS or other causes) calls for an increase in the ventilation pressure to force the needed fresh air into the lungs to overcome the inability of the lungs to function property, thus preventing the reduced oxygenation. However, if the ventilation pressure is raised too high, the excess pressure causes damage to the lungs, may lead to development of ARDS, and/or may increase the severity of the ARDS. The value of the transpulmonary pressure aids in setting the correct ventilation pressure in an attempt to achieve the balance between delivering sufficient oxygen to the lunge and preventing damage to the lungs.

A least some implementations of the systems, methods, apparatus, and/or code instructions described herein relate to the technical problem of monitoring for development of ARDS and/or predicting increasing severity of ARDS, before the onset of ARDS and/or before the increasing severity of ARDS. In contrast, it is noted that other systems are based on performing measurements only after the patient has already shown signs of breathing problems, indicating that ARDS has already developed and/or existing ARDS has increased in severity. Other systems that are based on dedicated esophageal pressure measurement catheters are installed only when a breathing problem is suspected. Moreover, insertion of the dedicated esophageal pressure measurement catheters into the esophagus when a feeding tube is already installed in the esophagus is problematic.

A least some implementations of the systems, methods, apparatus, and/or code instructions described herein relate to the technical problem of sensing transpulmonary pressure while a feeding tube is in use for feeding the patient, without removal of the feeding tube.

A least some implementations of the systems, methods, apparatus, and/or code instructions described herein relate to the technical problem of safely measuring esophageal wall pressure as an indicator of pleural pressure for estimating transpulmonary pressure. Other systems use a dedicated catheter based balloon designed for esophageal pressure measurements that is inflated once by a syringe, and the balloon is held in the inflated state for as long as required to monitor the esophageal pressure. Such continuous inflation may damage the esophageal wall. In contrast, some implementations of systems, methods, apparatus, and/or code instructions described herein address the technical problem by periodically inflating the balloon to measure the esophageal wall pressure, and then deflating the balloon. The balloon may be kept in the deflated state for a longer time interval than in the inflated state.

A least some implementations of the systems, methods, apparatus, and/or code instructions described herein relate to the technical problem of improving accuracy of measurement of esophageal wall pressure as an indicator of pleural pressure for estimating transpulmonary pressure. The technical problem is addressed by the periodic inflation and deflation of the esophageal body (e.g., balloon), which renews the pressure of the esophageal body. The renewed balloon pressure increases the accuracy of the measured esophageal wall pressure, by preventing errors due to leakage of fluid out of the inflated balloon that may occur over time. In contrast, other systems that are based on monitoring esophageal pressure over time by a constantly inflated balloon on a dedicated catheter are prone to measurement errors due to naturally dropping pressures occur over time.

In a further implementation form of the first, and second aspects, the system further comprises code instructions for and/or the method further comprises detecting a gastric reflux event based on an analysis of at least one impedance value measured by at least one impedance sensor located on a distal end of the feeding tube, and code for generating instructions for inflating the at least one esophageal body in response to the detected gastric reflux event.

In a further implementation form of the first, and second aspects, the system further comprises code instructions for and/or the method further comprises sensing an estimated amount of lung fluid in at least one lung of the target individual based on an analysis of at least one impedance value measured by at least one impedance sensor located on a distal end of the feeding tube, and code for generating instructions for periodically inflating the at least one esophageal body for periodic monitoring of the amount of lung fluid.

In a further implementation form of the first, and second aspects, the system further comprises code instructions for and/or the method further comprises computing a trend curve according to a plurality of esophageal wall pressures measured over a plurality of ventilation cycles for each periodic inflation of the at least one esophageal body, wherein each ventilation cycle mechanically performs inhalation and exhalation for the target individual, and wherein the transpulmonary pressure is estimated according to the trend curve.

In a further implementation form of the first, and second aspects, the system further comprises code instructions for and/or the method further comprises computing a trend curve according to a plurality of transpulmonary pressures measured over a historical time interval, and predicting a future transpulmonary pressure at a future time interval according to the trend curve.

In a further implementation form of the first, and second aspects, the system further comprises code instructions for and/or the method further comprises generating an alert for presentation on a display of a client terminal when the future transpulmonary pressure at the future time interval is predicted to increase above a threshold transpulmonary pressure.

In a further implementation form of the first, and second aspects, the system further comprises code instructions for and/or the method further comprises computing an estimate of a value of a Young modulus indicative of lung wall elasticity according to the computed transpulmonary pressure.

In a further implementation form of the first, and second aspects, the system further comprises code instructions for and/or the method further comprises computing a work of breathing (WOB) according to the computed transpulmonary pressure.

In a further implementation form of the first, and second aspects, the system further comprises code instructions for and/or the method further comprises presenting within a GUI, a pressure-volume graph depicting the WOB computed for the target individual and a reference WOB curve estimated for normal functioning lungs.

In a further implementation form of the first, and second aspects, the system further comprises code instructions for and/or the method further comprises presenting within a GUI, a trend curve indicative of a plurality of WOB values measured over a historical period of time.

In a further implementation form of the first, and second aspects, the system further comprises code instructions for and/or the method further comprises predicting a future WOB value at a future time interval based on an analysis of a plurality of historical computed WOB values.

In a further implementation form of the first, and second aspects, the system further comprises code instructions for and/or the method further comprises inflating the at least one esophageal body to according to a predefined volume.

In a further implementation form of the first, and second aspects, the feeding tube includes an enteral feeding tube having a distal end designed for positioning within the digestive system when in use for enteral feeding.

In a further implementation form of the first, and second aspects, the feeding tube includes a nasogastric tube having a distal end designed for positioning within the digestive system when in use.

In a further implementation form of the first, and second aspects, the feeding is sized and shaped for being disposed within the esophagus so that at least a distal end thereof is in the stomach lumen of a patient while at least one segment including the at least one esophageal body is placed in the esophagus of the patient.

In a further implementation form of the first, and second aspects, the at least one esophageal body is located within about 0-5 centimeters from the lower esophageal sphincter (LES) when inflated and contacting the inner wall of the esophagus.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 13 is a schematic depicting a simple model of mechanical ventilation of lungs of a target individual, and a mathematical representation for computation of the Young modulus for estimation of lung stiffness, in accordance with some embodiments of the present invention.

DETAILED DESCRIPTION

Figure 1:
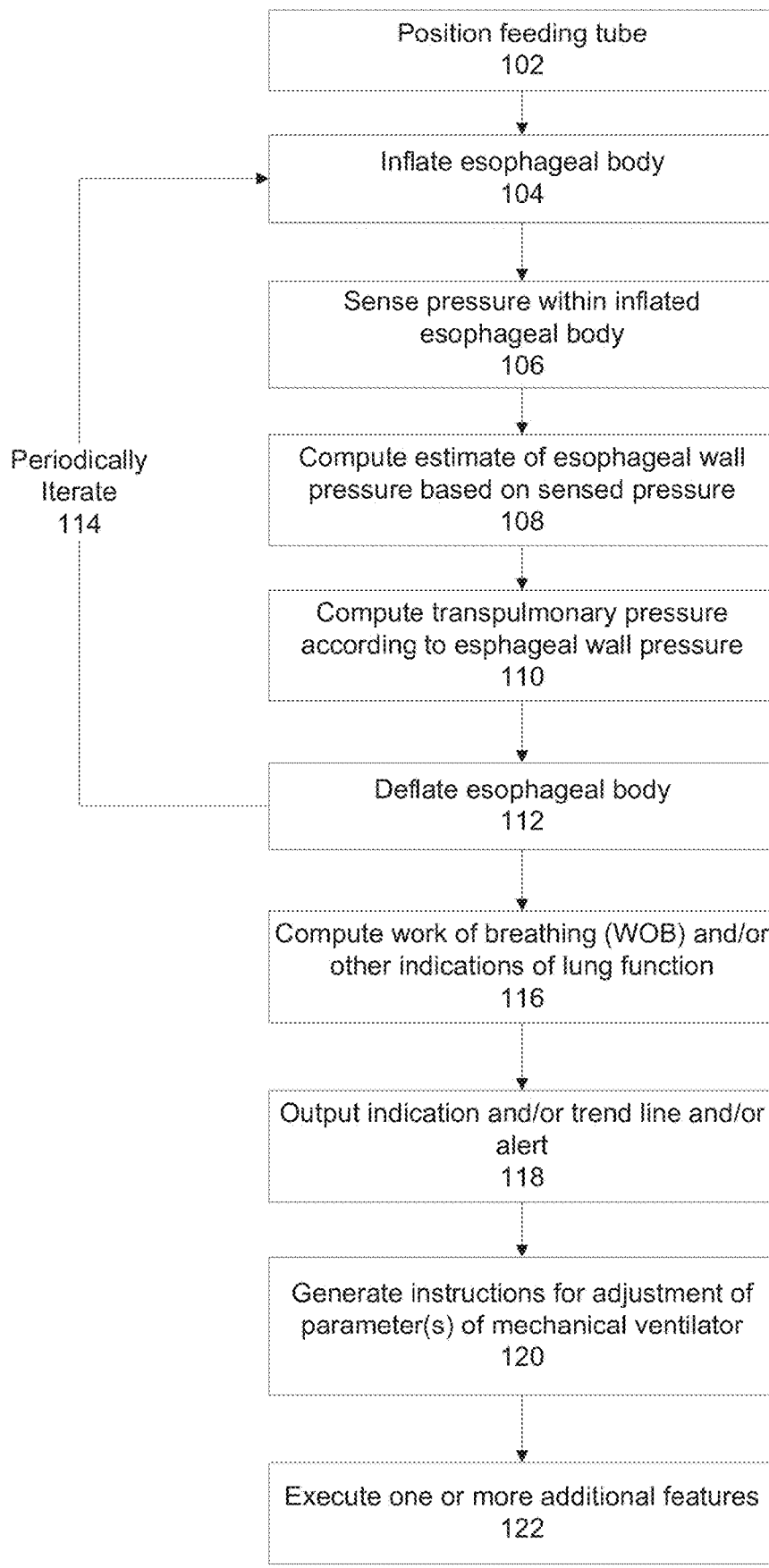
FIG. 1 is a flowchart of a method for monitoring a transpulmonary pressure of a mechanically ventilated target individual for adjustment of parameter(s) of a mechanical ventilator without removal of a feeding tube, in accordance with some embodiments of the present invention.

The present invention, in some embodiments thereof, relates to intra-body measurements and, more specifically, but not exclusively, to systems and methods for measurement of lung transpulmonary pressure.

An aspect of some embodiments of the present invention relates to a system for monitoring a transpulmonary pressure of a mechanically ventilated target individual for adjustment of parameter(s) of a mechanical ventilator that automatically mechanically ventilates the target individual according to the computed transpulmonary pressure, while the feeding tube is in place without removal of the feeding tube. The monitoring of the transpulmonary pressure and adjustment of parameters of the mechanical ventilator may be performed for prevention of or treatment of acute respiratory distress syndrome (ARDS). The system includes a feeding tube designed for insertion into a distal end of an esophagus of the mechanically ventilated patient. An esophageal body (or bodies) (e.g., balloon) having a pressure dependent volume is coupled to the distal portion of the feeding tube. The esophageal body is designed to contact the inner wall of the esophagus when inflated. A pressure sensor that senses pressure in the esophageal body measures the pressure at least when the esophageal body contacts the inner wall of the esophagus. Code instructions stored in a data storage device, when executed by one or more hardware processors, compute an estimation of esophageal wall pressure of the esophagus according to the pressure in the inflated esophageal body contacting the inner wall of the esophagus. The transpulmonary pressure of the mechanically ventilated target individual is computed according to the esophageal wall pressure. The esophageal body is periodically inflated and deflated for periodic monitoring of the transpulmonary pressure of the mechanically ventilated target patient while the feeding tube is in use. Instructions for adjustment of parameter(s) of a mechanical ventilator that automatically mechanically ventilates the target individual are computed according to the computed transpulmonary pressure. The instructions for adjustment of the parameter(s) of the mechanical ventilator are computed while the feeding tube is in place without removal of the feeding tube.

An aspect of some embodiments of the present invention relates to a method for monitoring a transpulmonary pressure of a mechanically ventilated target individual for adjustment of parameter(s) of a mechanical ventilator that automatically mechanically ventilates the target individual according to the computed transpulmonary pressure, while the feeding tube is in place without removal of the feeding tube. The monitoring of the transpulmonary pressure and adjustment of parameters of the mechanical ventilator may be performed for prevention of or treatment of acute respiratory distress syndrome (ARDS). A feeding tube is inserted into a distal end of an esophagus of the mechanically ventilated patient. An esophageal body (or bodies) (e.g., balloon) having a pressure dependent volume is coupled to the distal portion of the feeding tube. The esophageal body is designed to contact the inner wall of the esophagus when inflated. Esophageal wall pressure of the esophagus is estimated according to the pressure in the inflated esophageal body contacting the inner wall of the esophagus. The transpulmonary pressure of the mechanically ventilated target individual is computed according to the esophageal wall pressure. The esophageal body is periodically inflated and deflated for periodic monitoring of the transpulmonary pressure of the mechanically ventilated target patient while the feeding tube is in use. Instructions for adjustment of parameter(s) of a mechanical ventilator that automatically mechanically ventilates the target individual are computed according to the computed transpulmonary pressure. The instructions for adjustment of the parameter(s) of the mechanical ventilator are computed while the feeding tube is in place without removal of the feeding tube.

A least some implementations of the systems, methods, apparatus, and/or code instructions described herein relate to the technical problem of preventing the development of acute respiratory distress syndrome (ARDS) and/or treating ARDS in a target individual based on monitoring of transpulmonary pressure of the target individual. In particular, continuously (or near continuously, for example, at closely spaced intervals, for example, every minute, 5 minutes, or 10 minutes) monitoring the transpulmonary pressure. The transpulmonary pressure is measured in order to assess the correct amount of ventilation pressure to provide to a ventilated patient in order to ensure that the alveoli of the lungs receive sufficient oxygen without causing damage to the lungs. For example, the lungs in patients with ARDS do not function properly, and therefore require additional ventilation pressure for properly oxygenation. The improper functioning of the lung may occur for other reasons than ARDS, For example, in some patients abdominal organs may press against the diaphragm and the lungs cavity, thus resisting the respiration and hence reducing the blood oxygenation by the alveoli, even though the mechanical ventilation machine displays a sufficient airway pressure. The common medical practice for treatment of patients with abnormally functioning lungs (e.g., due to ARDS or other causes) calls for an increase in the ventilation pressure to force the needed fresh air into the lungs to overcome the inability of the lungs to function property, thus preventing the reduced oxygenation. However, if the ventilation pressure is raised too high, the excess pressure causes damage to the lungs, may lead to development of ARDS, and/or may increase the severity of the ARDS. The value of the transpulmonary pressure aids in setting the correct ventilation pressure in an attempt to achieve the balance between delivering sufficient oxygen to the lunge and preventing damage to the lungs.

A least some implementations of the systems, methods, apparatus, and/or code instructions described herein relate to the technical problem of monitoring for development of ARDS and/or predicting increasing severity of ARDS, before the onset of ARDS and/or before the increasing severity of ARDS. In contrast, it is noted that other systems are based on performing measurements only after the patient has already shown signs of breathing problems, indicating that ARDS has already developed and/or existing ARDS has increased in severity. Other systems that are based on dedicated esophageal pressure measurement catheters are installed only when a breathing problem is suspected. Moreover, insertion of the dedicated esophageal pressure measurement catheters into the esophagus when a feeding tube is already installed in the esophagus is problematic.

A least some implementations of the systems, methods, apparatus, and/or code instructions described herein relate to the technical problem of sensing transpulmonary pressure while a feeding tube is in use for feeding the patient, without removal of the feeding tube.

A least some implementations of the systems, methods, apparatus, and/or code instructions described herein relate to the technical problem of safely measuring esophageal wall pressure as an indicator of pleural pressure for estimating transpulmonary pressure. Other systems use a dedicated catheter based balloon designed for esophageal pressure measurements that is inflated once by a syringe, and the balloon is held in the inflated state for as long as required to monitor the esophageal pressure. Such continuous inflation may damage the esophageal wall. In contrast, some implementations of systems, methods, apparatus, and/or code instructions described herein address the technical problem by periodically inflating the balloon to measure the esophageal wall pressure, and then deflating the balloon. The balloon may be kept in the deflated state for a longer time interval than in the inflated state.

A least some implementations of the systems, methods, apparatus, and/or code instructions described herein relate to the technical problem of improving accuracy of measurement of esophageal wall pressure as an indicator of pleural pressure for estimating transpulmonary pressure. The technical problem is addressed by the periodic inflation and deflation of the esophageal body (e.g., balloon), which renews the pressure of the esophageal body. The renewed balloon pressure increases the accuracy of the measured esophageal wall pressure, by preventing errors due to leakage of fluid out of the inflated balloon that may occur over time. In contrast, other systems that are based on monitoring esophageal pressure over time by a constantly inflated balloon on a dedicated catheter are prone to measurement errors due to naturally dropping pressures occur over time.

A least some implementations of the systems, methods, apparatus, and/or code instructions described herein improve the performance of existing feeding tubes which are positioned with the esophagus of the patient for delivering enteral feedings to the stomach and/or digestive system of the patient. An inflatable element (e.g., balloon) which his used to prevent refluxing gastric contents from ascending along the esophagus may be used to measure esophageal wall pressure which provides an estimate of transpulmonary pressure.

A least some implementations of the systems, methods, apparatus, and/or code instructions described herein do not simply perform automation of a manual procedure, but perform additional automated features which cannot be performed manually by a human using pencil and/or paper. According to current practice, measurement of transpulmonary pressure may be performed by insertion of a dedicated catheter into the esophagus when the patient is suspected as having reduced lung function, for example, due to ARDS. The dedicated catheter may be inserted in response to clinical signs and/or symptoms of the patient, when reduced lung function has already occurred. Monitoring the development of reduced lung function, prior to the onset of the reduced lung function and/or prior to increasing severity of the lung function, according to current practice is difficult, unreliable, and generally not performed. Moreover, current method are based on measuring current transpulmonary pressure, and do not relate to prediction of future transpulmonary pressure. In contrast, some implementations of the systems, methods, apparatus, and/or code instructions described herein provide real-time, optionally continuous, monitoring of transpulmonary pressure, and/or optionally predict a risk of excessive transpulmonary pressure and/or a risk of transpulmonary pressure that is too low. An indication of the monitoring and/or prediction may be generated, which provides healthcare workers with early and/or advanced notification for taking preventing action and/or early treatment to avoid complications and/or consequences of delayed diagnosis and treatment.

When the features related to by the systems, methods, apparatus, and/or code instructions described herein are taken as a whole, the combination of the features amounts to significantly more than a simple mathematical calculation of computing transpulmonary pressure and/or computation of values based on the transpulmonary pressure (e.g., work of breathing (WOB)). The systems, methods, apparatus, and/or code instructions described herein do not merely relate to mathematical computations (e.g., equations), but relate to the particular data collected, stored, and the way the data is collected by pressure sensors, and optionally performing a prediction of likelihood of exceeding a target transpulmonary pressure in the near future.

A least some implementations of the systems, methods, apparatus, and/or code instructions described herein improve an underlying technical process within the technical field of mechanical ventilation.

A least some implementations of the systems, methods, apparatus, and/or code instructions described herein provide a unique, particular, and advanced technique of adjustment of parameters of a mechanical ventilator.

A least some implementations of the systems, methods, apparatus, and/or code instructions described herein are tied to physical real-life components, for example, one or more of: pressure sensor(s) that measure pressure, an inflatable body (e.g., balloon), a feeding tube (e.g., nasogastric tube, enteral feeding tube), computational hardware (e.g., hardware processor(s), physical memory device) that analyzes the output of the pressure sensor, a mechanical ventilator, and a display.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the terms esophageal body and balloon may sometimes be interchanged. It is noted that the balloon is an exemplary implementation of the esophageal body, however other implementations are possible.

The concept of transpulmonary pressure is now briefly discussed. Transpulmonary pressure is the difference between alveolar pressure and pleural pressure. The esophageal wall pressure may be used as an indication of an estimate of the pleural pressure. Therefore, the pressure difference between the alveolar pressure and the esophageal wall pressure is indicative of the pressure difference between the airway pressure and the esophageal pressure, which is indicative of the transpulmonary pressure.

As described herein, the pressure within the inflated balloon is used as an indicator of the esophageal wall pressure.

Transpulmonary pressure is indicative of the health status of the lungs. The value of the transpulmonary pressure measured for a target individual is used to customized the ventilation parameters of a ventilation machine to help make sure that sufficient gas exchange occurs in the alveoli of the lungs of the target patient.

Figure 2:
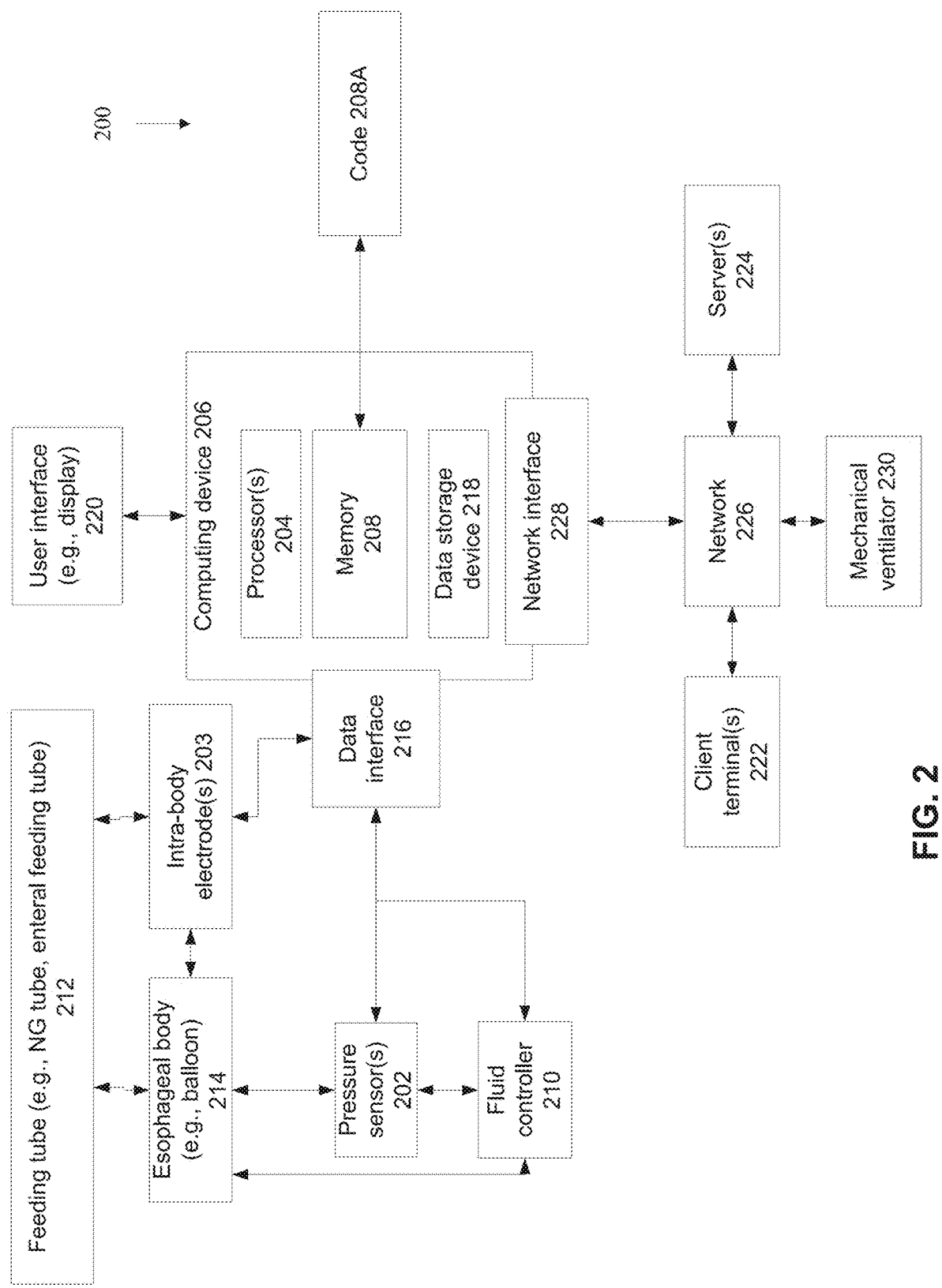
FIG. 2 is a block diagram of a system for monitoring a transpulmonary pressure of a mechanically ventilated target individual for adjustment of parameter(s) of a mechanical ventilator without removal of a feeding tube, in accordance with some embodiments of the present invention.

Reference is now made to FIG. 1, which is a flowchart of a method for monitoring a transpulmonary pressure of a mechanically ventilated target individual for adjustment of parameter(s) of a mechanical ventilator without removal of a feeding tube, optionally for prevention of or treatment of acute respiratory distress syndrome (ARDS), in accordance with some embodiments of the present invention. Reference is also made to FIG. 2, which is a block diagram of a system 200 for monitoring a transpulmonary pressure of a mechanically ventilated target individual for adjustment of parameter(s) of a mechanical ventilator without removal of a feeding tube, optionally for prevention of or treatment of acute respiratory distress syndrome (ARDS), in accordance with some embodiments of the present invention. One or more of the acts of the method described with reference to FIG. 1 may be implemented by components of system 200, as described herein, for example, by a processor(s) 204 of a computing device 206 executing code instructions 208A stored in a memory 208 (also referred to herein as a data storage device).

A feeding tube 212 is implemented as an enteral feeding tube for feeding the patient. The enteral feeding tube is positioned within the gastrointestinal system of the patient, for example, within the stomach, duodenum, or upper small intestine. The transpulmonary pressure of mechanically ventilated patients being enterally fed may be monitored without requiring insertion of an additional probe, since the enteral feeding tube is already positioned within the esophagus for feeding the patient. The enteral feeding tube provides an additional function of monitoring the transpulmonary pressure of the patient.

Alternatively or additionally, feeding tube 212 is implemented as a nasogastric (NG) tube for evacuation of contents from the stomach. The NG tube is positioned within the gastrointestinal system of the patient, for example, within the stomach, duodenum, or upper small intestine. The transpulmonary pressure of mechanically ventilated patients having their stomach contents being drained and/or stomach maintained in a drained state may be monitored without requiring insertion of an additional probe, since the NG tube is already necessary to treat the patient.

Feeding tube 212 includes one or more esophageal bodies 214, optionally elastic, located on the distal end of feeding tube 212, for example, an inflatable balloon(s). Esophageal body 214 may be designed to be inflated, for example, in response to identification of an indication of reflux, and/or for sensing lung fluid of the patient. In one example, when inflated, esophageal body 214 contacts the inner wall of the esophagus, preventing or reducing refluxing digestive (e.g., stomach) contents from ascending via the esophagus. The indication of reflux may be detected, for example, by an analysis of impedance values measured by an electrode(s) 203 located within the esophagus, for example, at the distal end of feeding tube 212. Additional details of an exemplary implementation of feeding tube 212 and esophageal body 214 that is inflated in response to identification of reflux may be found with reference to U.S. Pat. No. 9,226,878, to common inventors and the same assignee. The contents of U.S. Pat. No. 9,226,878 are incorporated herein by reference in their entirety.

A pressure sensor 202 senses the pressure in the esophageal body 214. Pressure sensor 202 at least senses the pressure when esophageal body 214 is inflated is and contacting the inner wall of the esophagus. Pressure sensor 202 may continuously sense the pressure within esophageal body 214, for example, for controlling the inflation and/or deflation of the esophageal body.

A fluid controller 210 delivers fluid for inflating esophageal body 214. Fluid controller 210 may evacuate the fluid out of esophageal body 214 for deflation of esophageal body 214. Fluid controller 210 may be implemented as, for example, one or more pumps, valve(s), fluid syringe(s), and/or combinations of the aforementioned.

Exemplary fluids for inflation of esophageal body 214 include: liquids (e.g., saline, water), and/or gases (e.g., oxygen, nitrogen, carbon dioxide).

Computing device 206 may communicate with pressure sensor(s) 202 and/or fluid controller(s) 210 via one or more data interfaces 216, for example, a network interface, a wire connection, a wireless connection, a local bus, other physical interface implementations, and/or virtual interfaces (e.g., software interface, application programming interface (API), software development kit (SDK)).

Computing device 206 may be implemented as, for example, a standalone integral unit, a virtual machine, a client terminal, a server, a computing cloud, a mobile device, a desktop computer, a thin client, a Smartphone, a Tablet computer, a laptop computer, a wearable computer, glasses computer, and a watch computer. Computing device 206 may be implemented as a customized unit that include locally stored software and/or hardware that perform one or more of the acts described with reference to FIG. 1. Alternatively or additionally, computing device 206 may be implemented as code instructions loaded on an existing computing device. Alternatively or additionally, computing device 206 may be implemented as hardware and/or code instructions (e.g., an accelerator card) installed and/or integrated within an existing computing device.

Processor(s) 204 of computing device 206 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 204 may include one or more processors (homogenous or heterogeneous), which may be arranged for parallel processing, as clusters and/or as one or more multi core processing units. Processor(s) 204 may be hardware processors.

Memory 208 stores code instructions executable by processor(s) 204. Memory 208 is implemented as, for example, a random access memory (RAM), virtual memory, read-only memory (ROM), and/or a storage device, for example, non-volatile memory, magnetic media, semiconductor memory devices, hard drive, removable storage, and optical media (e.g., DVD, CD-ROM). Memory 208 stores code instructions 208A that implement one or more acts of the method described with reference to FIG. 1. Alternatively or additionally, one or more acts of the method described with reference to FIG. 1 are implemented in hardware.

Code instructions 208A may perform one or more features described with reference to act 122 of FIG. 1, for example: detect a gastric reflux event based on an analysis of impedance value(s) measured by impedance sensor(s) (e.g., electrodes 203) located on a distal end of the feeding tube, and optionally one or more externally located electrodes. Instructions may be generated for automatically inflating the esophageal body in response to the detected gastric reflux event. Alternatively or additionally, code instructions 208A may sense an amount of lung fluid in the lungs of the target individual based on impedance value(s) measured by impedance sensor(s) (e.g., electrodes 203) located on a distal end of the feeding tube, and optionally one or more externally located electrodes. Instructions may be generated for automatically periodically inflating the esophageal body for periodic sensing of the amount of lung fluid.

Computing device 206 may include a data storage device 218 for storing data, for example, a history of estimated transpulmonary pressure values and/or estimated work of breathing (WOB) values. Data storage device 218 may be implemented as, for example, a memory, a local hard-drive, a removable storage unit, an optical disk, a virtual memory, a storage device, and/or as a remote server and/or computing cloud (e.g., accessed via a network connection).

Computing device 206 includes and/or is in communication with a user interface 220 that includes a mechanism for a user to enter data (e.g., patient information) and/or view presented data (e.g., estimated transpulmonary pressure, trend of WOB). Exemplary user interfaces 220 include, for example, one or more of, a touchscreen, a gesture device, a display, a keyboard, a mouse, and voice activated software using speakers and microphone. External devices, such as client terminals 222 and/or server(s) 224 communicating with computing device 206 over a network 226 may serve as user interface 220, for example, a smartphone running an application may establish communication (e.g., cellular, network, short range wireless) with computing device 206 over network 226 using a communication interface (e.g., network interface, cellular interface, short range wireless network interface). The user may enter data and/or view data on the display of the smartphone, optionally via a graphical user interface (GUI) application.

Computing device 206 may be in communication with client terminal(s) 222 and/or server(s) 224 over network 226 via a network interface 228. Network interface 228 may be implemented as, for example, a network interface card, a hardware interface card, a wireless interface, a physical interface for connecting to a cable, a virtual interface implemented in software, communication software providing higher layers of connectivity, and/or other implementations.

Client terminal(s) 222 and/or server(s) 224 may receive indications and/or alerts generated by computing device 206, for example, currently computed estimate of transpulmonary pressure, computed trend of transpulmonary pressure, warning that the transpulmonary pressure reached a defined threshold, and/or a prediction warning that the trend of the transpulmonary pressure is indicating an impending significant mismatch in the parameters of the mechanical ventilation machine. Exemplary client terminal(s) 222 include: a mobile device, a smartphone, a tablet computer, a remotely located personal computer, a glasses computer, and a watch computer. Exemplary server(s) 224 include: a hospital medical record server (e.g., the transmitted data may be automatically logged into the patient electronic medical record), and/or a remote monitoring station (e.g., nurses station that monitors multiple patients on the ward).

Computing device 206 may be in communication via network 226 with a mechanical ventilator 230 that mechanically ventilates the target individual. Instructions for adjustment of mechanical ventilator 230 that are automatically generated by computing device 206 may be transmitted over 226 to mechanical ventilator 230.

Referring now back to FIG. 1, at 102, the feeding tube 212 is inserted via the esophagus, into a distal end of an esophagus of a target patient mechanically ventilated by ventilator 230. The feeding tube 212 may be sized and shaped for being disposed within the esophagus so that at least a distal end of the feeding tube 212 is in the stomach lumen of the mechanically ventilated patient, while the segment(s) that include the esophageal body is placed in the esophagus of the patient, optionally the lower portion of the esophagus, for example, above and in proximity to the lower esophageal sphincter (LES), for example, without about 0-3, or about 0-5, or about 0-10 centimeters of the LES, or other values.

The feeding tube 212 may be an oral tube inserted via the mouth, and/or a nasogastric tube inserted via the nose. The distal end of the feeding tube 212 is designed for positioning within the digestive system when in use for enteral feeding.

The feeding tube 212 is inserted for feeding a mechanically ventilated target individual, and for monitoring the target individual for example, for prevention of or treatment of acute respiratory distress syndrome (ARDS).

At 104, the esophageal body 214 of feeding tube 212 is inflated. The esophageal body 214 may be automatically inflated by the fluid controller 210 according to instructions generated by the computing device 206. The esophageal body 214 is automatically inflated to a target pressure, and/or according to a target volume. Fluid controller 210 may deliver gas (e.g., nitrogen, oxygen, air, carbon dioxide) and/or liquid (e.g., saline, water), optionally compressed to a target pressure for inflation of esophageal body 214.

The inflation may be performed at a controlled inflation rate. The inflation may be performed to reach the target pressure and/or target volume.

Figure 3:
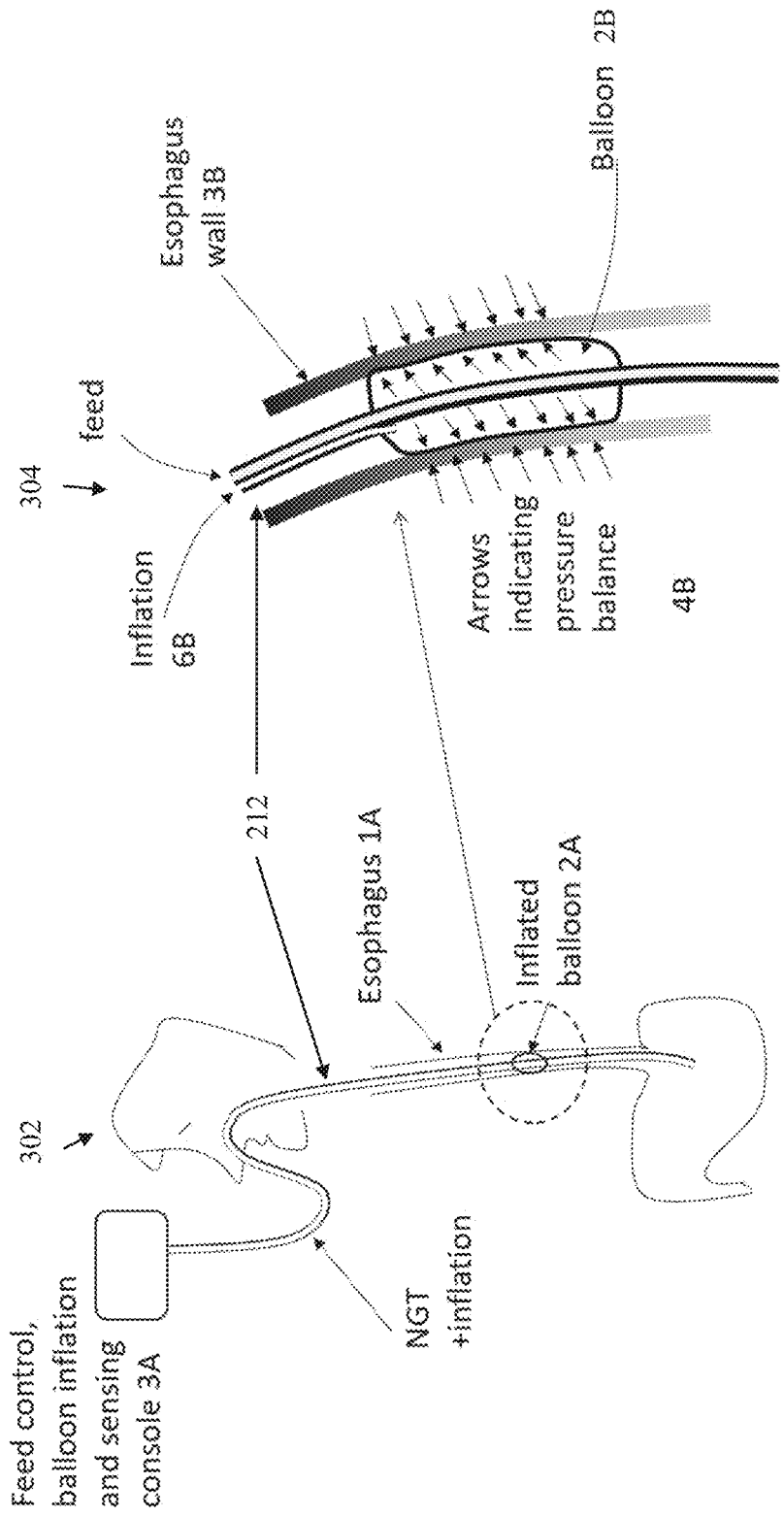
FIG. 3 is a schematic depicting a feeding tube within an esophagus of a patient, and a schematic depicting pressure balance between a balloon of a feeding tube and an esophagus wall, in accordance with some embodiments of the present invention.

Reference is now made to FIG. 3, which includes a schematic 302 depicting feeding tube 212 within esophagus 1A of the patient, and a schematic 304 depicting pressure balance between balloon 5B of feeding tube 212 and esophagus wall 3B, in accordance with some embodiments of the present invention. Components described with reference to FIG. 3 may correspond to components of system 200 described with reference to FIG. 2. Inflated balloon 2A is inflated by admitting fluid via a tube (e.g., capillary tube) 6B that runs adjacent to a feeding lumen of the feeding tube 212. A feed controller 3A performs the inflation, optionally at a set inflation volume rate (denote Q) and/or senses pressure within inflated balloon 2A. Arrows 4B indicate a pressure balance between the forced applied by esophagus wall 3B on inflated balloon 2B and between the force applied by inflated balloon 2B on esophagus wall 3B. The pressure balance enables estimation of the pressure difference between the lung pressure and the esophageal wall pressure.

Figure 4:
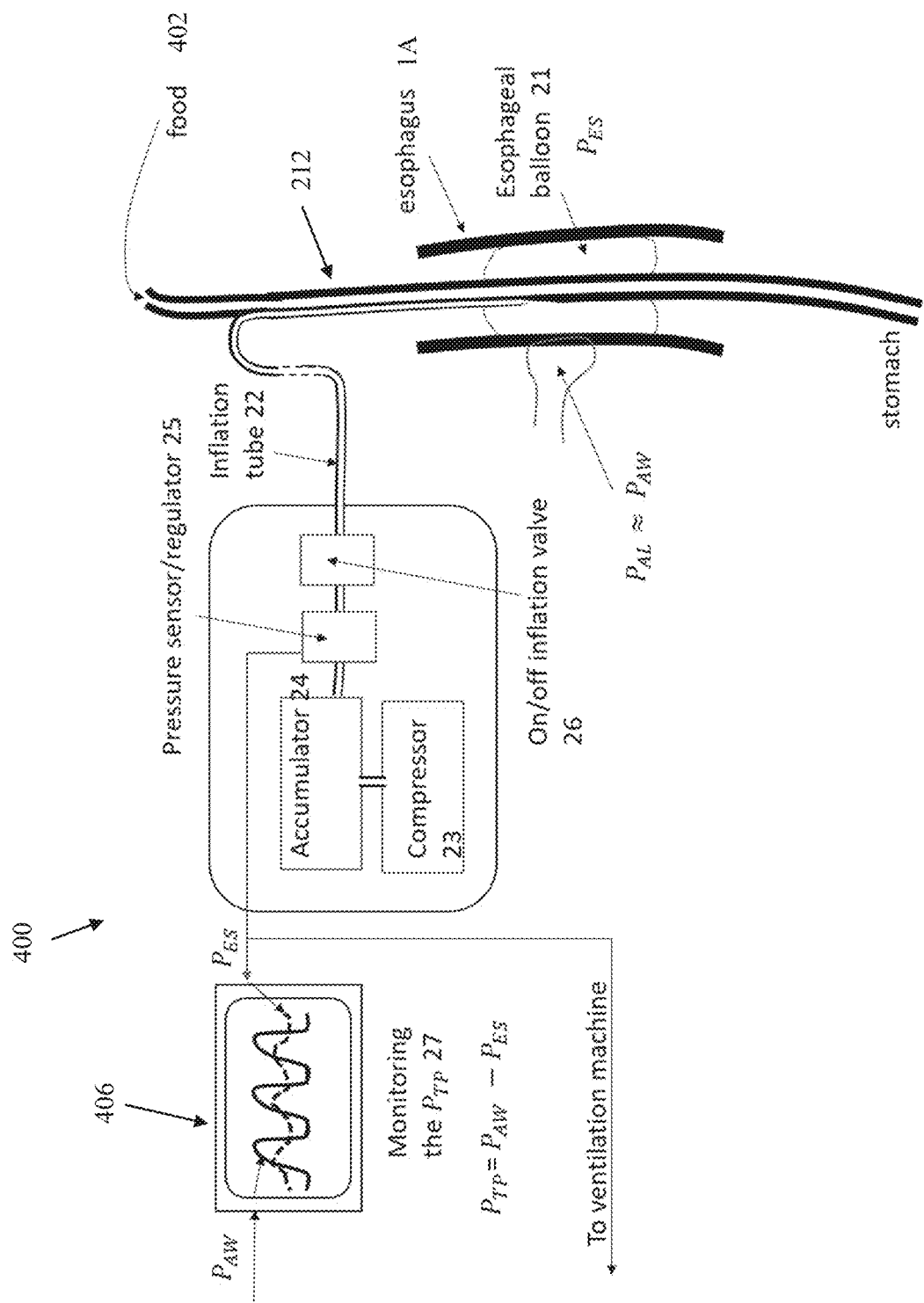
FIG. 4 is a block diagram of components of an exemplary architecture for regulating and/or monitoring pressure within an esophageal balloon deployed within the esophagus, in accordance with some embodiments of the present invention.

Reference is now made to FIG. 4, which is a block diagram of components of an exemplary architecture 400 for regulating and/or monitoring pressure within an esophageal balloon 21 deployed within esophagus 1A, in accordance with some embodiments of the present invention. Components of exemplary architecture 400 may be based on and/or correspond to components of system 200 described with reference to FIG. 2.

Pressure within esophageal balloon 21 (denoted $P_{ES}$) is controlled and/or monitored by one or more of the following components: a compressor 23 for generating compressed fluid (e.g., gas, liquid) to a target pressure. An accumulator 24 for storing the compressed fluid. A pressure sensor/regulator 25 for sensing and/or regulating the pressure within esophageal balloon 21. An on/off inflation valve 26 for by insertion the compressed fluid into esophageal balloon 21 and/or removal of the compressed fluid from esophageal balloon 21. An inflation tube 22 connected to feeding tube 212 directed the fluid into esophageal balloon 21 for inflation thereof, and/or directs fluid out of esophageal balloon 21 for deflation thereof. Optionally, inflation tube 22 is a lumen that is separate from a main lumen of feeding tube 212 through which food 402 is delivered. For example, inflation tube 22 may be located in parallel to the main tube, for example, within the wall of the main tube.

Optionally, a computing device 406 receives data from pressure sensor/regulator 25 indicative of real-time pressure within esophageal balloon 21, indicative of the esophageal wall pressure, denoted $P_{ES}$. Computing device 406 may receive from the mechanical ventilation machine (and/or from another computing device) an indication of a real-time pressure within the airway of the patient, denoted $P_{AW}$.

The transpulmonary pressure denoted $P_{TP}$ may be computed as the difference between the airway pressure and the esophageal wall pressure, denoted $P_{TP} = P_{AW} - P_{ES}$. The values of one or more of $P_{TP}$, $P_{AW}$, and $P_{ES}$ may be plotted on a display, optionally in real-time, as graphs. The graphs depict fluctuations due to the artificial inspiration and expiration performed by the mechanical ventilation machine. Computing device 406 (and/or another device) may communicate measurements of the transpulmonary pressure and/or the esophageal pressure back to the ventilation machine for manual and/or automatic adjustment of the ventilation machine, for example, to obtain a target airway pressure.

Referring now back to FIG. 1, at 106, the pressure within esophageal body 214 is sensed. The pressure is sensed at the target volume and/or to confirm the target pressure. The pressure within esophageal body 214 may be sensed when the target volume and/or target pressure is reached, while esophageal body 214 remains inflated. The measurement of the pressure within esophageal body 214 may be terminated and/or ignored right before deflation of esophageal body 214.

At 108, an estimate of esophageal wall pressure of the esophagus is computed. The esophageal wall pressure may be estimated according to the pressure in the esophageal body when the esophageal body is inflated to the target pressure and/or volume and is contacting the inner wall of the esophagus.

It is noted that the esophageal wall pressure is modulated according to the ventilation cycle (i.e., artificial inspiration and expiration) administered by the ventilation machine to the target individual. The modulation is in addition to the gas exchange occurring in the alveoli.

It is noted that excess pressure on the lungs by the diaphragm may affect the esophagus, by increasing the pressure on the esophageal wall, similarly to excess pressure in the lungs. The esophageal wall pressure may be used as an indication of the required ventilation to overcome the pressure by the diaphragm.

At 110, the transpulmonary pressure of the mechanically ventilated target individual is computed according to the esophageal wall pressure. The transpulmonary pressure is computed as the difference between the airway pressure delivered by the mechanical ventilation machine, and the esophageal wall pressure. The transpulmonary pressure represents the component of the airway pressure delivered by the mechanical ventilation machine that actually inflates the alveoli within the lungs.

The transpulmonary pressure may be computed for an equilibrium state, in which the pressure applied by the inflated balloon on the esophageal wall is balanced by (and/or approximately equal to) the pressure applied by the lung tissue (i.e., alveoli pressure) on the esophageal wall.

In terms of mathematical representation, at equilibrium, when the balloon is inflated to the target pressure and/or target volume, the pressure applied by the balloon on the esophageal wall relates to the pressure applied by the lungs (i.e., alveoli pressure) on the esophageal wall and is denoted as $\Delta P_{AL} \propto \Delta P_B$. $P_{AL}$ denotes the pressure applied by the lungs (i.e., alveoli pressure) on the esophageal wall and $P_B$ denotes the pressure applied by the balloon on the esophageal wall. Based on the assumption that $P_{AW} \cong P_{AL}$ and $P_{ES} = P_B$, where $P_{AW}$ denotes airway pressure, and $P_{ES}$ denotes esophageal pressure, monitoring pressure changes within the balloon by the pressure sensor is indicative of stiffness of the lung tissue as indicated by the transpulmonary pressure (difference) denoted $P_{TP}$, which is computed as $P_{TP}=P_{AW}-P_{ES}$.

Figure 5:
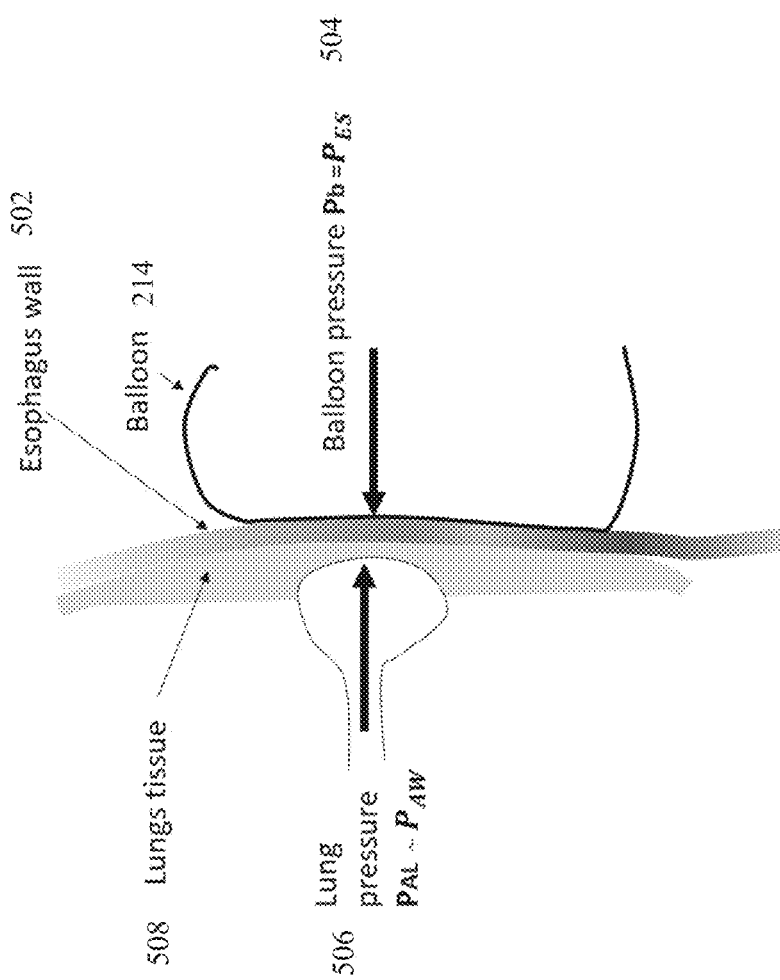
FIG. 5 is a schematic depicting an esophageal wall at a state of pressure balance between pressure applied by the inflated balloon on esophageal wall and lung pressure applied by lung tissue on the esophageal wall, in accordance with some embodiments of the present invention.

Reference is now made to FIG. 5, which is a schematic depicting an esophageal wall 502 at a state of pressure balance between pressure 506 applied by inflated balloon 214 on esophageal wall 502 and lung pressure 504 applied by lung tissue 508 on esophageal wall 502, in accordance with some embodiments of the present invention. As discussed above, based on the assumption that $P_{AW} \cong P_{AL}$ and $P_{ES}=P_B$, $P_{TP}=P_{AW}-P_{ES}$.

Figure 6:
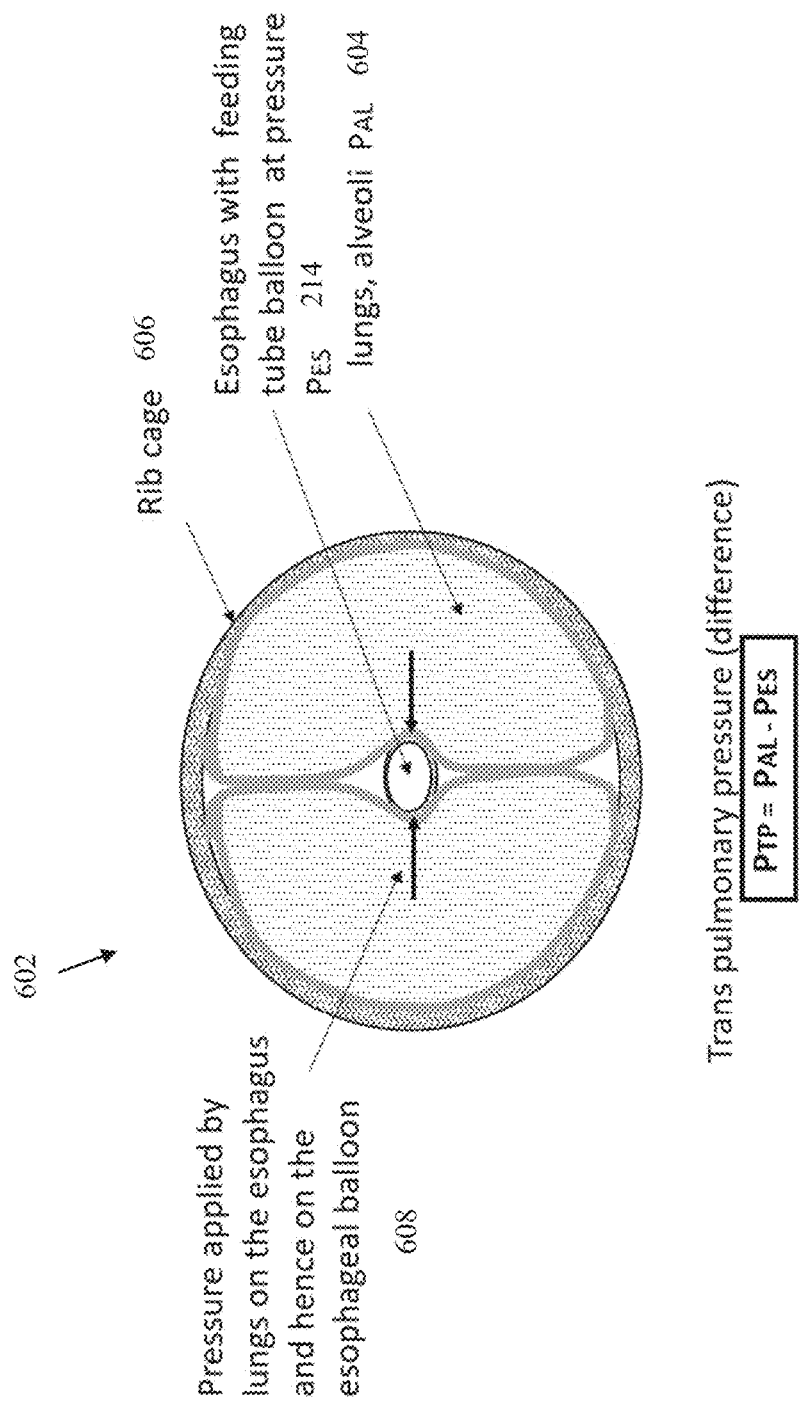
FIG. 6 is a schematic of a cross section of the thorax of the target individual depicting the location of esophageal body in the inflated state relative to the lungs, in accordance with some embodiments of the present invention.

Reference is now made to FIG. 6, which is a schematic of a cross section of the thorax of the target individual 602 depicting the location of esophageal body 214 in the inflated state relative to lungs 604, in accordance with some embodiments of the present invention. Cross section may be taken at approximately the T7 level, or at other anatomical locations where esophageal body 214 is located along the feeding tube. Lungs 604, which are contained by a rib cage 606 apply a pressure 608 on the esophagus, which is transmitted to pressure by the inner wall to the esophagus applied to the inflated balloon 214. Alveoli pressure within the lungs 504 is denoted $P_{AL}$. Pressure within the balloon 214, when inflated, is indicative of esophageal wall pressure denoted $P_{ES}$. The transpulmonary pressure denoted $P_{TP}$ may be computed as the difference between the alveoli pressure in the lungs and the esophageal wall pressure, denoted $P_{TP}=P_{AW}-P_{ES}$.

Optionally, the transpulmonary pressure is computed over multiple ventilation cycles. The transpulmonary pressure may be computed, for example, as an average of multiple transpulmonary pressures computed over the multiple ventilation cycles (e.g., sampling the airway pressure and the esophageal pressure at multiple points during inhalation and exhalation performed by the ventilation machine), and/or as a least square fit of the multiple transpulmonary pressures.

Referring now back to FIG. 1, at 112, the inflated esophageal body 214 is deflated, optionally by fluid controller 210. Deflation of esophageal body 214 removes pressure from the esophageal wall, preventing damage to the esophageal wall that might otherwise occur from prolonged application of pressure by the inflated balloon. For example, prolonged application of pressure by the inflated balloon may disturb blood circulation in the esophageal wall, leading to necrosis.

Figure 7:
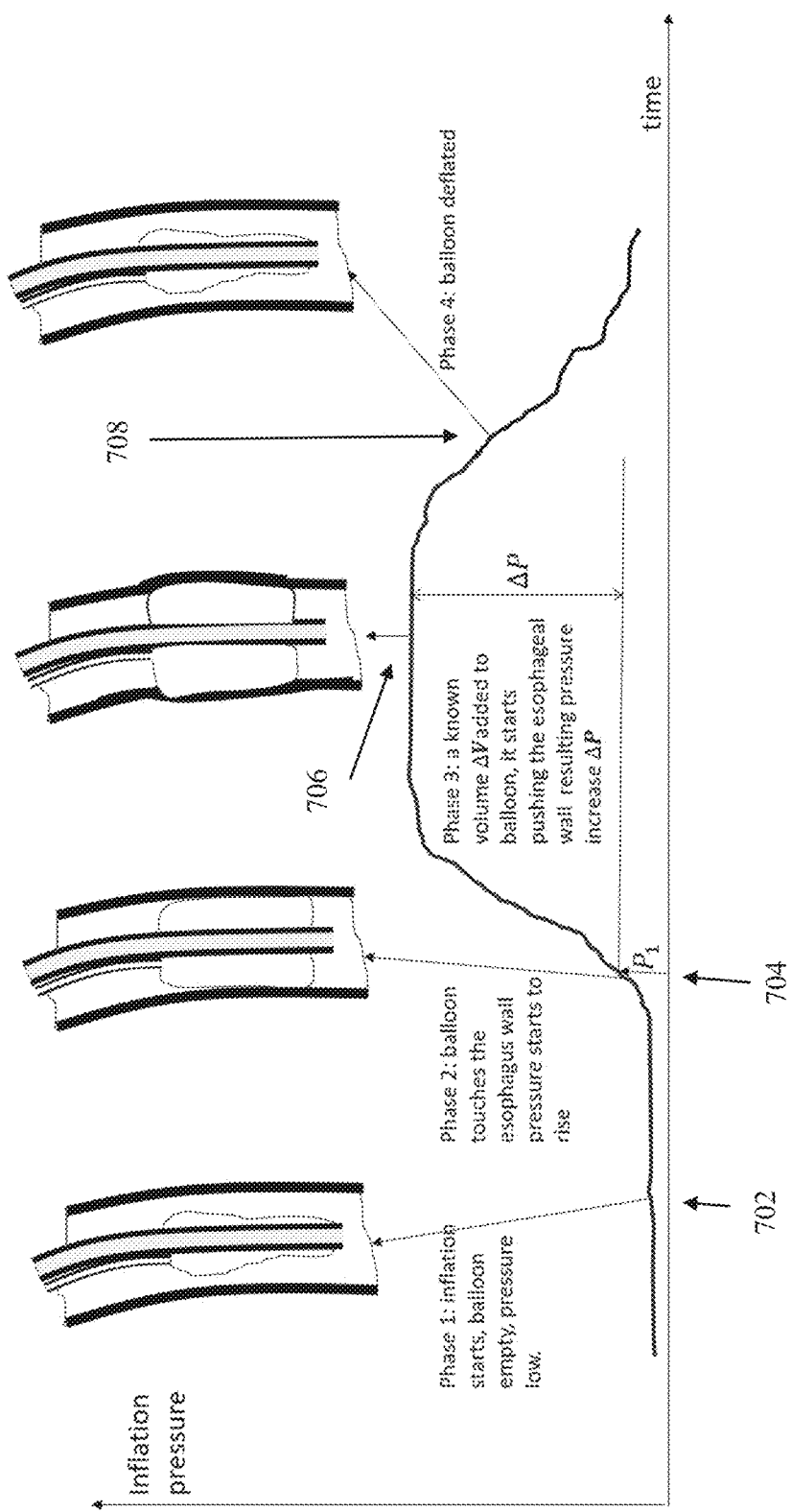
FIG. 7 is a graph depicting inflation pressure of the esophageal body over time for a monitoring cycle, in accordance with some embodiments of the present invention.

Reference is now made to FIG. 7, which is graph depicting inflation pressure of the esophageal body over time for a monitoring cycle, in accordance with some embodiments of the present invention. At 702, the esophageal body is in the deflated state. The balloon is relatively empty and the pressure is relatively low. Inflation of the balloon is started. At 704 (also denoted as $P_1$) the inflating balloon contacts the inner wall of the esophagus. Pressure rises within the balloon as inflation continues. At 706, a selected volume (denoted $\Delta V$) has been inserted into the balloon. Alternatively, the volume is inserted into the balloon until a selected pressure is reached (denoted $P_B$). The balloon, which is resisted against volume expansion by the esophageal wall, experiences an increase in pressure (denoted $\Delta P$). The rise in pressure may be mathematically represented as:

$$P_{es}=P_B=P_1+\Delta P(t_1)$$

At 708, the balloon is deflated.

Figure 8:
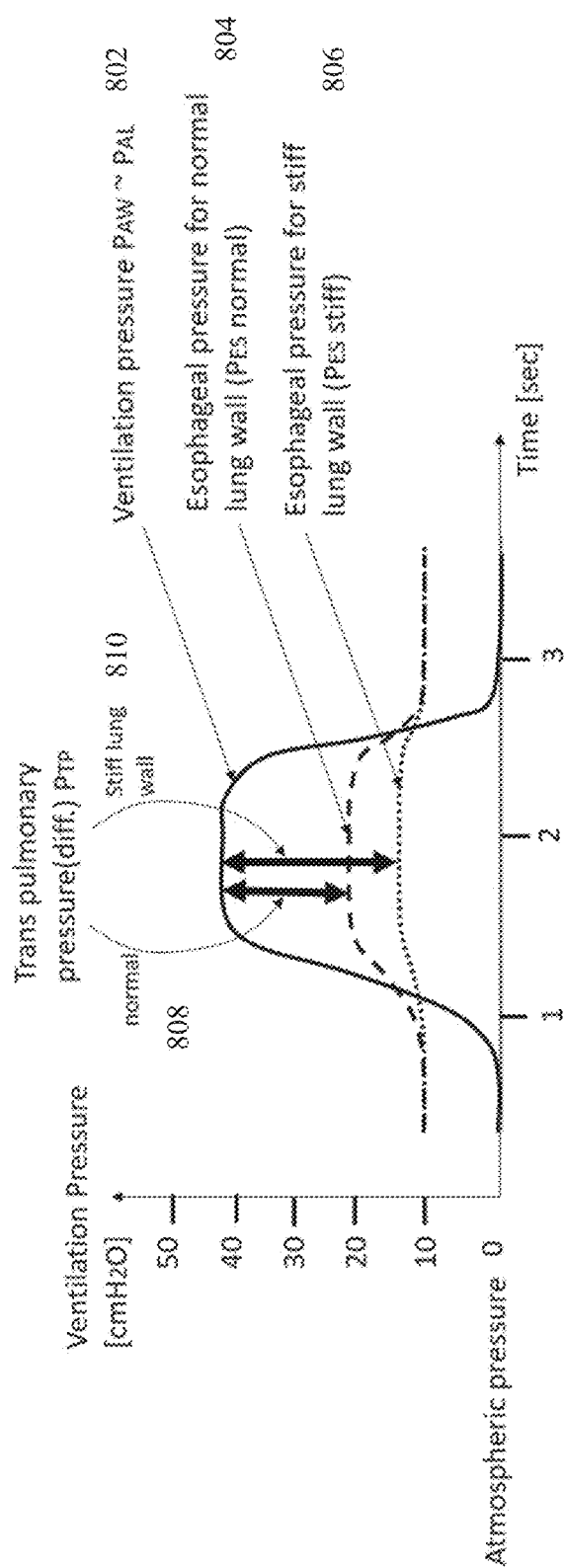
FIG. 8 is a graph depicting an example of a ventilation pressure applied by a ventilation machine, an example of a normal esophageal pressure for normal lung wall tissue, and an example of esophageal pressure for stiff lung wall tissue over a single ventilation cycle, in accordance with some embodiments of the present invention.

Reference is now made to FIG. 8, which is a graph depicting an example of a ventilation pressure 802 applied by a ventilation machine, an example of a normal esophageal pressure for normal lung wall tissue 804, and an example of esophageal pressure for stiff lung wall tissue 806 (e.g., as occurs in ARDS) over a single ventilation cycle (along the x-axis denoting time), in accordance with some embodiments of the present invention. Ventilation pressure 802 may be mathematically denoted as $P_{AW} \cong P_{AL}$, as described herein. Transpulmonary pressure ($P_{TP}$) is computed for the normal lung as the difference between the ventilation pressure and the esophageal pressure for the normal lung wall ($P_{ES}$ normal) 808. Transpulmonary pressure ($P_{TP}$) is computed for the stiff lung as the difference between the ventilation pressure and the esophageal pressure for the stiff lung wall ($P_{ES}$ stiff) 810. It is noted that $P_{TP}$ computed for the stiff lung is greater than $P_{TP}$ for the normal lung. As such, monitoring for increasing values of transpulmonary pressure and/or for a transpulmonary pressure above a threshold is indicative of development of lung conditions associated with lung stiffening, for example, onset of ARDS and/or increasing severity of ARDS.

Referring now back to FIG. 1, at 114, one or more acts 104-112 are iterated for periodically inflating and deflating the esophageal body 214. The inflation is periodically performed for periodic monitoring of the transpulmonary pressure of the mechanically ventilated target patient while the feeding tube 212 is in use.

The iterations for monitoring the transpulmonary pressure are executed while the feeding tube is in place and in use for feeding the patient, without removal of the feeding tube.

Each monitoring period is based on a cycle of inflation of balloon 214, maintaining the balloon 214 in an inflated and equilibrium state for a certain period of time over which one or more ventilation cycles (i.e., artificial inhalation and exhalation) are administered by the ventilation machine, deflation of balloon 214, and a period of time in which the balloon 214 remains deflated. Each monitoring period may be defined from the start of the currency inflation cycle of balloon 214 until the next inflation cycle of balloon 214.

Each monitoring period may be, for example, about 30 seconds, 1 minute, 5 minute, 10 minutes, or time intervals. The measurement interval during each monitoring period when the transpulmonary pressure is measured (i.e., when balloon 214 is held in the inflated state) is, for example, about 5, 10, 15, 20, or 30 seconds, or other values. The interval during each monitoring period may be represented as a duty cycle of the monitoring period, for example, about 1%, 5%, 10%, or 25%, or other values.

Figure 9:
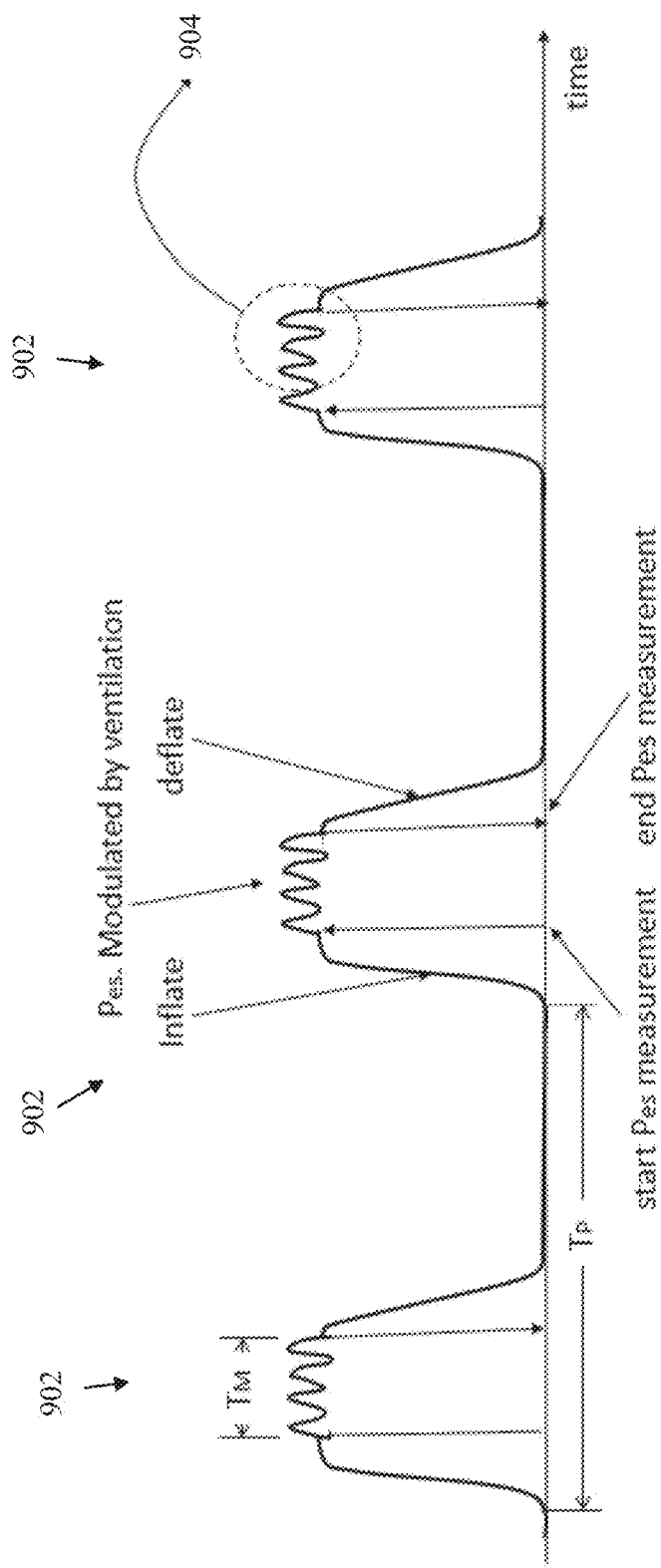
FIG. 9 is a schematic depicting multiple monitoring periods, in accordance with some embodiments of the present invention.

Reference is now made to FIG. 9, which is a schematic depicting multiple monitoring periods 902, in accordance with some embodiments of the present invention. The length of each monitoring period is denoted $T_P$. The measurement interval is denoted $T_M$. The start of the measurement interval is denoted $P_{es}$. It is noted that the esophageal pressure denoted Pes (represented by the pressure within inflated balloon 214) is modulated according to the ventilation cycles administered by the ventilation machine. A blow-up of the modulation of Pes, depicted by 904 is shown with reference to FIG. 10.

Referring now back to 114 of FIG. 1, optionally, the transpulmonary pressure is computed over multiple monitoring periods. The transpulmonary pressure may be computed, for example, as an average of the multiple transpulmonary pressures computed over the multiple monitoring g periods, where each monitoring period includes multiple ventilation cycles, and/or as a least square fit of the multiple transpulmonary pressures over the multiple monitoring periods.

Optionally, the trend line is plotted on a display (e.g., within a GUI).

The trend line may be analyzed automatically by code and/or visually (i.e., manually) by a user to distinguish between transpulmonary pressure changes that occur over relatively short intervals (e.g., less than about 1 second, or 5 seconds, or 1 minute, or 5 minutes, or other values) and changes that occur over relatively longer intervals (e.g., longer than about 10 minutes, or 30 minutes, or 60 minutes, or other values). Pressure changes occurring over relatively long time intervals may be due to onset of ARDS and/or worsening of patient condition (e.g., ARDS).

Pressure changes occurring over relatively short intervals may be due to non-medical reasons, for example, accidental movement of the tube, blockage within the tube, and/or erroneous changes in parameters of the ventilation machine.

Figure 10:
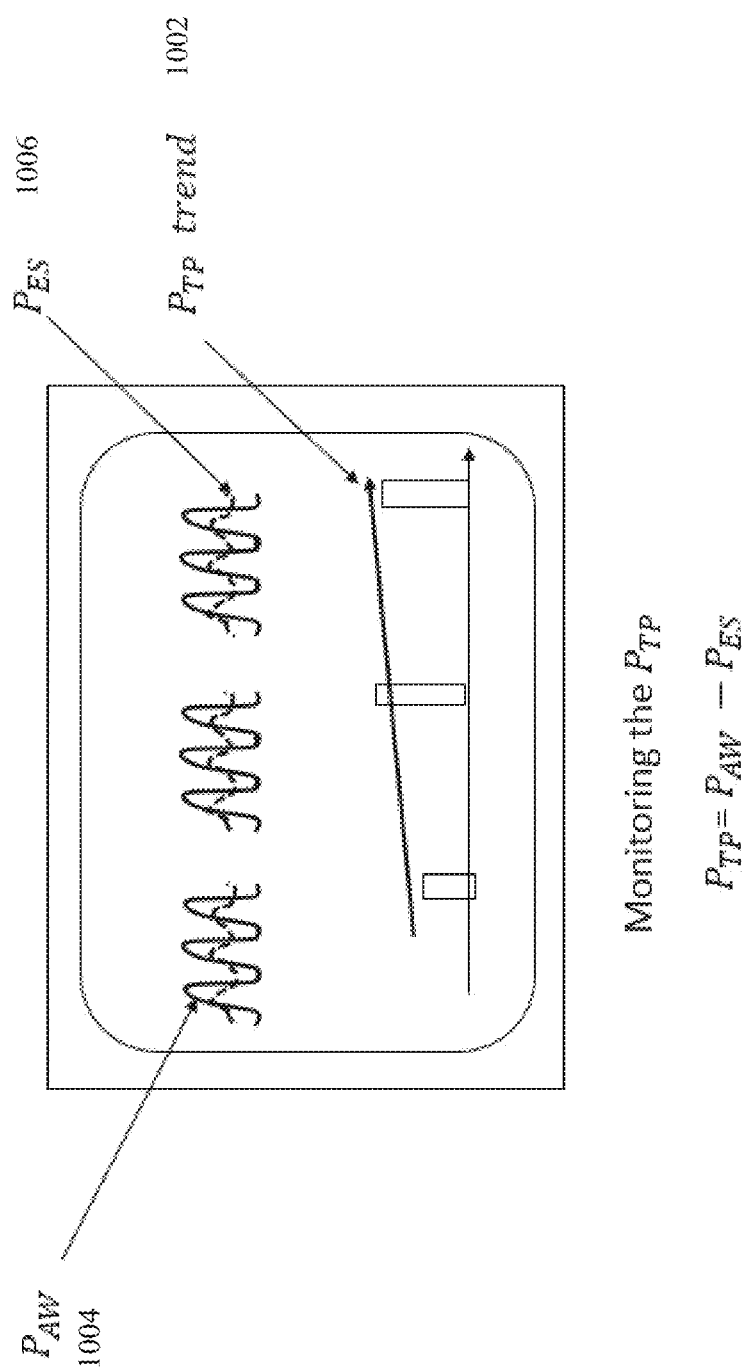
FIG. 10 is a schematic of a trend curve indicative of transpulmonary pressure computed over multiple monitoring periods, where each monitoring period includes multiple ventilation cycles, in accordance with some embodiments of the present invention.

Reference is now made to FIG. 10 which is a schematic of a trend curve 1002 indicative of transpulmonary pressure (denoted $P_{TP}$) computed over multiple monitoring periods, where each monitoring period includes multiple ventilation cycles, in accordance with some embodiments of the present invention. The trend curve may be computed, for example, as a least square fit of transpulmonary pressure values measured at different time intervals, and/or as an average of the transpulmonary pressure values. $P_{TP}$ is computed as the difference between points of a $P_{AW}$ curve 1004 indicative of the airway pressure which may be provided by the ventilation machine and points of a $P_{ES}$ curve 1006 indicative of the esophageal wall pressure computed according to the pressure within the balloon inflated within the esophagus. The $P_{TP}$ trend curve 1002 may be presented on a display of a client terminal and/or of the computing device, for example, within a GUI.

Referring now back to FIG. 1, at 116, a work of breathing (WOB) for the target individual is computed according to the computed transpulmonary pressure. The WOB may be computed as the area under a curve of transpulmonary pressure versus lung volume over a single mechanical ventilation cycle. The WOB may be indicative of the general status of the respiratory system of the patient. For example, an increasing WOB may be indicative of worsening condition of the patient. An increasing WOB may be indicative of changes to the parameters of the mechanical ventilation machine to offset the worsening condition in order to deliver sufficient oxygen to the target individual.

Optionally, a graph of volume versus pressure is presented within a GUI on a display, for example, of a client terminal. The pressure-volume graph depicts the WOB computed for the target individual, and may present a reference WOB curve estimated for normal functioning lungs, and/or may present a WOB curve computed for the target individual during an earlier time interval. The comparison between the curve pressure-volume graph and the normal and/or early pressure-volume graph may visually indicative changes occurring to the target individual over time. For example, a user visually analyzing the pressure-volume graph may diagnose a stiffening of the lung wall.

Figure 11:
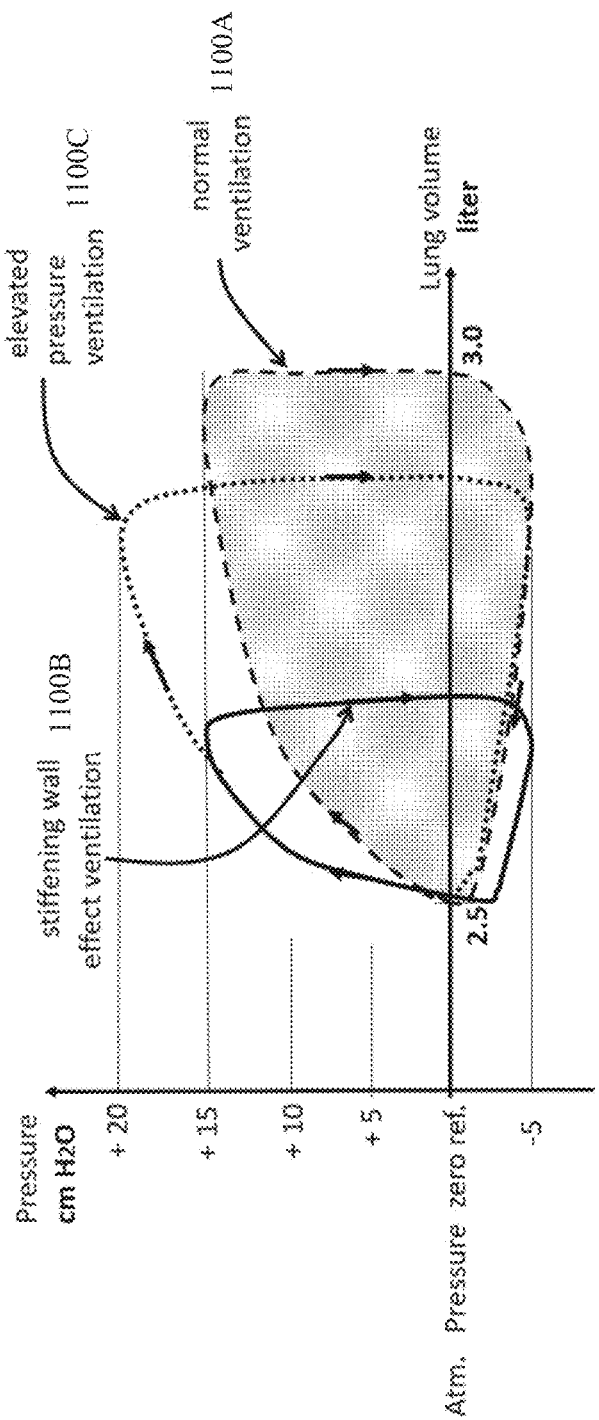
FIG. 11 is a schematic of pressure-volume curves indicative of WOB, in accordance with some embodiments of the present invention.

Reference is now made to FIG. 11, which depicts an example of pressure-volume curves 1100A-C indicative of WOB, in accordance with some embodiments of the present invention. Curves 1100A-C are plotted for one or more ventilation cycles, as transpulmonary pressures as a function of lung volume estimated according to the volume administered by the mechanical ventilation machine to the target individual. Curves 1100A-C may be presented within a GUI on a display of a client terminal. Curve 1100A may be presented as a reference curve indicative of normal ventilation for a ventilated individual with clinically insignificant lung wall stiffness. Patients having a curve similar to curve 1100A may be ventilated for example with 15 centimeters (cm) of H2O pressure to achieve a tidal volume of 0.5 liter. The reference curve may be presented within the GUI in addition to curves computed for the target individual, for example, using a different color and/or with a different label. Curve 1100B is an example of a pressure-volume curve for a patient experiencing a stiffening of the lung wall. Patients having similar curves cannot be fully ventilated with the ventilation parameters that are appropriate for patients having a curve similar to curve 1100A. For example, attempting a ventilation in a patient having a curve similar to curve 1100B with the pressure parameters appropriate for curve 1100A (e.g., 15 cm H20) obtains a lower tidal volume of 0.2 liters (instead of 0.5 liter). To compensate for the lost tidal volume, the pressure delivered by the mechanical ventilation machine may be increased, for example, to 20 cm H2O to obtain a tidal volume of 0.4 liter. Curve 1100C is an example of a pressure-volume curve for a patient being mechanically ventilated with an elevated ventilation pressure, for example, to compensate for the stiffening lung.

Referring now back to FIG. 1, at 116, a trend curve indicative of multiple WOB values measured over a historical period of time is presented within the GUI. The curve may be updated in real-time, as additional WOB values are computed.

Optionally, a future WOB value at a future time interval is predicted based on an analysis of the historical computed WOB values, optionally of the trend curve.

Figure 12:
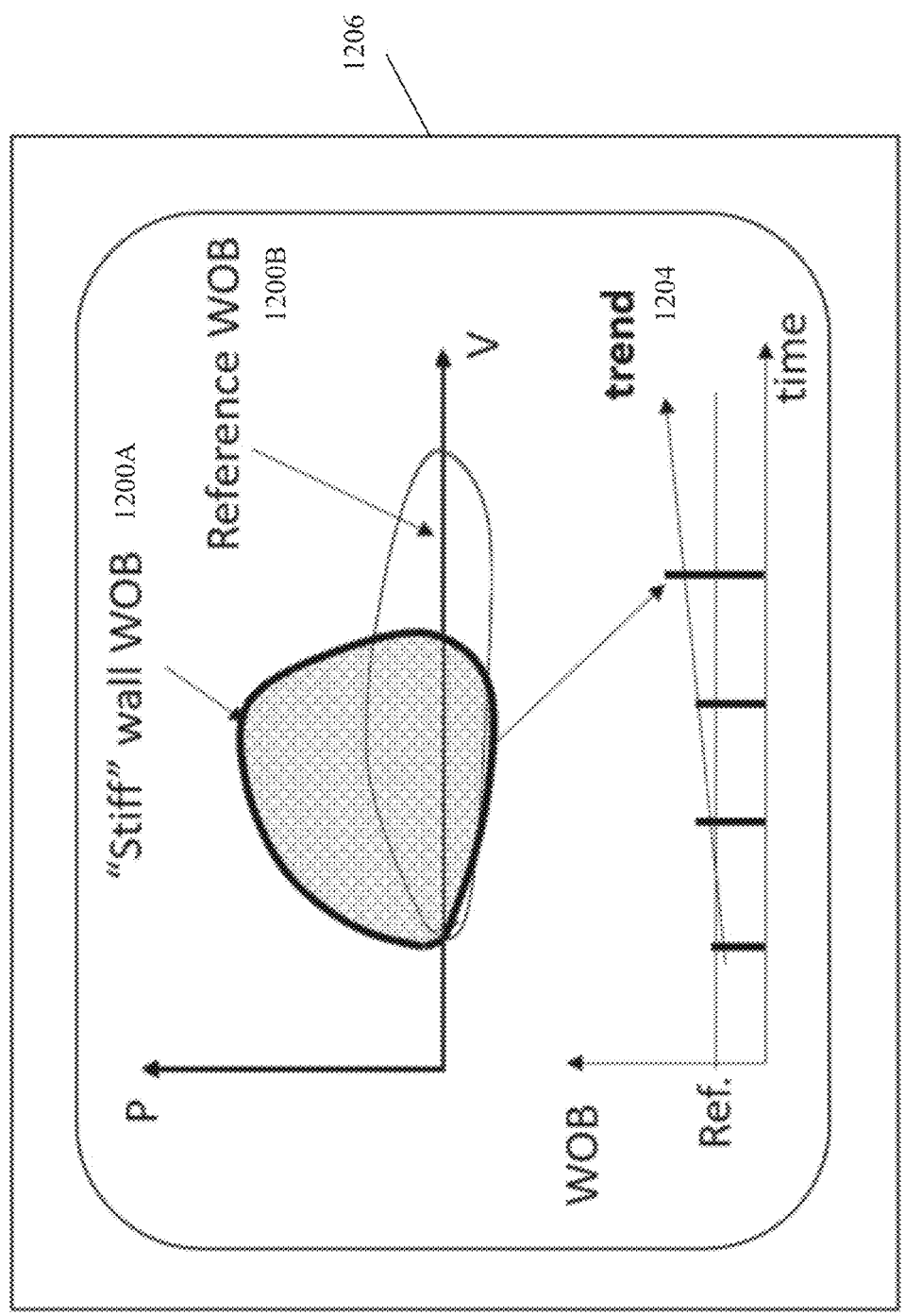
FIG. 12 is a schematic of a presentation of pressure-volume curve(s) indicative of WOB, in accordance with some embodiments of the present invention.

Reference is now made to FIG. 12 which is an example of a presentation of a pressure-volume curve(s) indicative of WOB 1200A-B, and a trend curve 1204 plotted according to multiple WOB values computed over a historical time interval, in accordance with some embodiments of the present invention. The presentation may be displayed within a GUI 1206 on a display of a client terminal. The pressure-volume curves may include a WOB curve computed for the target individual 1200A and optionally a reference WOB for normally functioning lungs 1200B, as described herein. The WOB curves 1200A-B may be dynamically updated in real-time according to real-time pressure-volume measurements, and the trend curve 1204 may be dynamically updated in real-time according to the WOB value corresponding to the real-time curve.

Referring now back to FIG. 1, at 116, optionally an estimate of a value indicative of lung wall elasticity is computed according to the computed transpulmonary pressure, optionally a value of a Young modulus of the lung wall. For example, the value (e.g., Young modulus) may be according to a scale of 0-1 (or other scales) where a value of 0 indicates normal lung stiffness and 1 indicates a very abnormally stiff lung.

Reference is now made to FIG. 13, which is a schematic 1302 depicting a simple model of mechanical ventilation of lungs of a target individual, and a mathematical representation 1304 for computation of the Young modulus for estimation of lung stiffness, in accordance with some embodiments of the present invention.

The ventilation machine, represented by piston P pushes a ventilation displacement volume $V_0$ into the lungs of the target individual during the forward stroke 1 to 2. As a result the lung volume expands from an initial volume denoted $V_1$ to a final volume denoted $V^2$ or $V_1+V_T$ and the initial pressure (e.g., at PEEP) $P_1$ increases by $\Delta P$ to reach a final pressure denoted $P_2$. The tidal volume $V_T$ may be expressed as $V_2-V_1$. The process may be assumed to be isothermal, which allows for application of Boyle's law (PV=Constant) and a representation according to the following equation:

$$(V_1+V_0)P_1=(V_1+V_T)(P_1+\Delta P)$$

Moreover, the lung wall elasticity may be approximated by a generalized Young modulus equation, where k denotes the Young modulus:

$$\Delta P = k\, V_T$$

The above two equations yield a formula for the Tidal volume $V_T$:

$$V_T = \frac{P_1 V_0}{P_1 + kV_1}$$

Calculating the isothermal work:

$$W_{12} = P_1(V_1 + V_0)\ln\frac{V_1 + V_T}{V_1 + V_0} + P_{atm}V_0$$

Where: $W_{ATM}=P_{atm}V_0$

The maximal work appears when the stiffness k is very large, almost "solid wall" with no compliance. This is the case when VT approaches zero to yield:

$$W_{12}(\max) = -0.1 P_1(V_1+V_0) + P_{atm}V_0 \cong 4[\text{joule}]$$

Neglecting the atmospheric work $-P_{atm}V_0$ since it always appears, the relative breathing work factor denoted r=(W12−$W_{ATM}$)/(W12(max)−$P_{atm}$) will be:

$$r = 10\text{abs}\left[\ln\frac{V_1 + V_T}{V_1 + V_0}\right]$$

For an example case of 300 milliliters (ml) tidal volume, 400 ml ventilator stroke and lung volume of 3 liter:

$$r=0.3$$

Since a healthy ideal lung has r=0 and a wall stiff lung (poor condition) has r=1 the example indicates lungs in reasonably good shape. Therefore, the r value is an indicator of the health of the lungs.

At 118, an alert may be generated. The alert may be triggered when the transpulmonary pressure is above a selected threshold and/or when a set of rules is met indicative of an impending target transpulmonary pressure, for example, a prediction that the transpulmonary pressure will excess the selected threshold in the future. The prediction may be performed according to the trend curve of transpulmonary pressures. The threshold for triggering the alert may be selected as the value of the transpulmonary pressure that is indicative of stiffening of lung tissue and/or indicative of onset of ARDS and/or increasing severity of ARDS.

The alert may be transmitted to another device, for example, of a client terminal, a mobile device, and a monitoring station server. The alert may, for example, presented on a screen, sent as an email and/or text message, and/or played as an audio message (e.g., audio file and/or phone call).

The alert may be triggered when the WOB is above a selected threshold and/or when a set of rules is met indicative of an impending target WOB value, for example, a prediction that the WOB will excess the selected threshold in the future.

Optionally, a trend curve is computed according to transpulmonary pressures measured over a historical time interval. A future transpulmonary pressure at a future time interval may be predicted according to the trend curve, for example, by extrapolation of the trend curve forwards in time, and/or by a statistical classifier trained according to the historical values. The alert may be generated when the prediction indicates that the transpulmonary pressure is expected to increase over the threshold during a predefined future time interval.

At 120, instructions for adjustment of parameters of the ventilation machine are automatically generated according to the computed transpulmonary pressure. Alternatively or additionally, the instructions for adjustment of parameters of the ventilation machine are automatically generated according to the computed WOB. The instructions may include instructions for adjustment the pressure of the gas and/or volume of the gas being administered by the ventilation machine.

The instructions for adjustment of the parameters of the ventilation machine are generated while the feeding tube is in place and in use for feeding the patient, without removal of the feeding tube.

The instructions may be transmitted to the ventilation machine for automatic adjustment thereof over network 226. The instructions may be presented on a display, for review by a user (e.g., attending physician, ventilation machine technician). The user may review the instructions and manually adjust the parameters of the ventilation machine and/or authorize the automatic adjustment of the parameters.

The instructions for adjustment of parameters of the ventilation machine may be computed based on additional data (e.g., received by computing device from one or more sensors and/or manually entered by users), for example, vital signs, oxygen saturation, and airway pressure.

Figure 14:
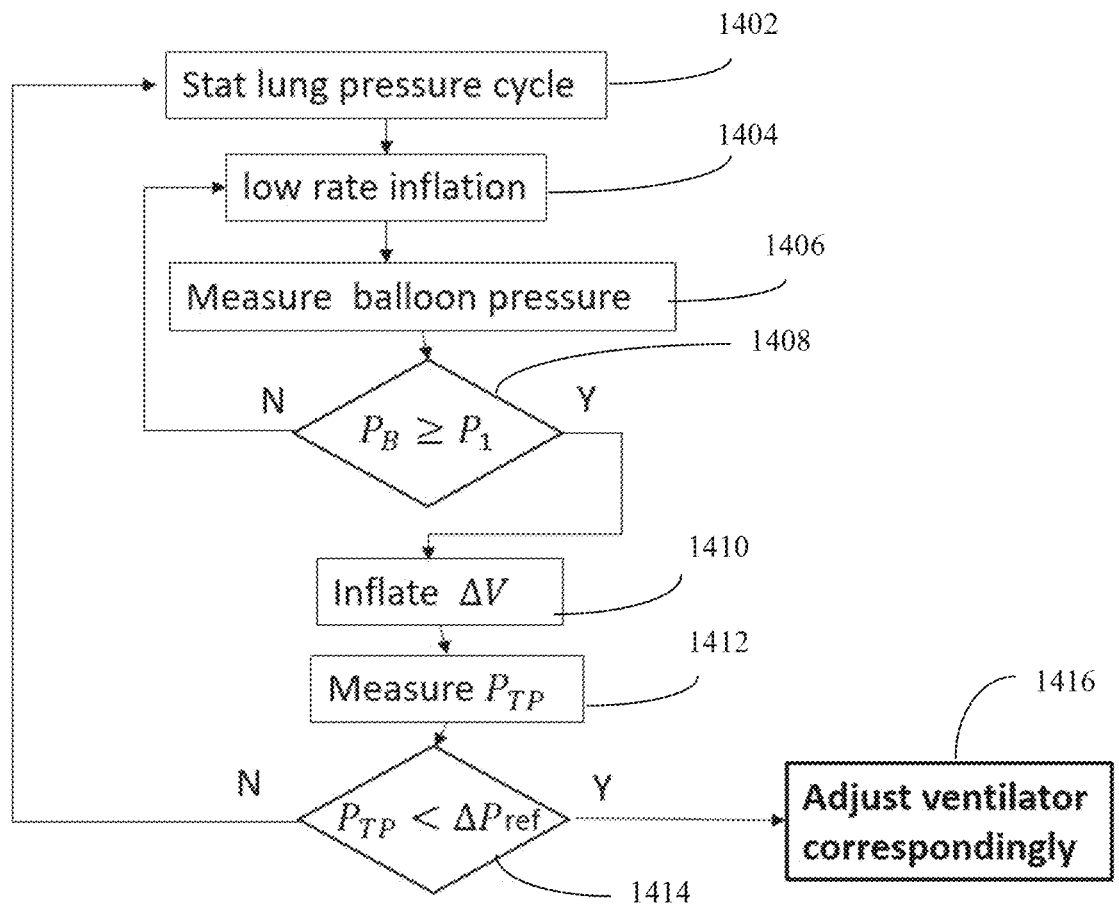
FIG. 14 is a flowchart of another process for sensing the transpulmonary pressure of a target individual for adjustment of mechanical ventilator ventilating the target individual, in accordance with some embodiments of the present invention.

Reference is now made to FIG. 14, which is a flowchart of another process for sensing the transpulmonary pressure of a target individual for adjustment of mechanical ventilator ventilating the target individual, in accordance with some embodiments of the present invention. The process described with reference to FIG. 14 is graphically illustrated by FIG. 7. The process described with reference to FIG. 14 may correspond to one or more acts of the methods described with reference to FIG. 1, and/or is implemented by one or more components of system 200 described with reference to FIG. 2.

At 1402, the current monitoring cycle starts. At 1404, the balloon located at the distal end portion of the feeding tube is slowly inflated at a controlled rate. At 1406, the balloon pressure is measured by a pressure sensor. At 1408, the sensed balloon pressure denoted $P_B$ is compared to an initial target pressure $P_1$. Acts 1404-1408 are iterated until the balloon pressure reaches or exceeds the target pressure. At 1410, a predefined volume denoted ΔV is inserted into the balloon. At 1412, the transpulmonary pressure denoted $P_{TP}$ is computed as described herein. At 1414, the current transpulmonary pressure is compared to a reference transpulmonary pressure. The reference transpulmonary pressure may represent a threshold indicating insufficient ventilation pressure. At 1416, when the current transpulmonary pressure is less than the reference transpulmonary pressure, the ventilator ventilating the target individual is adjusted accordingly, manually and/or automatically. When the current transpulmonary pressure is greater than the reference transpulmonary pressure, the balloon may be deflated until the next monitoring cycle.

Referring now back to FIG. 1, at 122, one or more additional features may be executed based on the impedance computed from sensors (e.g., electrodes) located on the balloon and/or the estimated pressure in the balloon. The same electrodes and/or balloon located on the feeding tube within the esophagus may perform one or more additional features, in addition to the estimation of the transpulmonary pressure:

Exemplary additional features include one or more of:

Estimating an amount of lung fluid in the patient. When inflated, electrode(s) 203 located on the surface of esophageal body 214 contacts the inner wall of the esophagus to measure electrical parameters (e.g., impedance) for estimating an amount of lung fluid in the patient. Additional details of an exemplary implementation of feeding tube 212 and esophageal body 214 that is inflated to sense lung fluid be found with reference to International Patent Application No. IB2017/057702, to the same inventors and the same assignee, the contents of which are incorporated herein by reference in their entirety.

Monitoring a position of the tube within the digestive system based on an analysis of the applied alternating current and measured voltage drop. For example, to detect when the tube moves out of the correct position. Impedance values sensed by electrode(s) 203 are analyzed for monitoring the position of the feeding tube 212 within the esophagus, for example, as described with reference to U.S. Pat. No. 9,713,579, by the same inventors of the present application, to the same inventors and the same assignee, the contents of which are incorporated herein by reference in their entirety.

Estimating a level of fluid within the digestive system based on an analysis of the applied alternating current and measured voltage drop. The enteral feeding rate delivered by the feeding tube may be automatically adjusted according to the estimated fluid level, for example, to prevent reflux. Additional details of exemplary systems and/or methods for estimating fluid levels based on impedance measurements computed based on electrode(s) located on a tube positioned within the esophagus may be found with reference to International Patent Application No. IL2015/051156, by the same inventors of the present application.

Detecting a gastric reflux event based on an analysis of the applied alternating current and measured voltage drop. For example, to stop enteral feeding. Optionally, when a gastric reflux event is detected, the estimation of lung fluid may be stopped and/or adjusted to account for the gastric reflux event, for example, by subtracting the computed impedance value (denoting total impedance due to lung fluid and reflux) from the estimated impedance value due to the presence of fluid in the esophagus due to the reflux. When no gastric reflux event is detected, the measured impedance may be assumed to be an indication of lung fluid without interference effects due to the presence of fluid within the esophagus (i.e., the reflux). Additional details of exemplary systems and/or methods for detecting reflux event based on impedance measurements computed based on electrode(s) located on a tube positioned within the esophagus may be found with reference to International Patent Application No. IL2017/050634, by the same inventors of the present application.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant nasogastric tubes and esophageal bodies will be developed and the scope of the terms nasogastric tubes and esophageal bodies are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for monitoring a transpulmonary pressure of a mechanically ventilated target individual, the system comprising:
   a feeding tube for insertion into a distal end of an esophagus of the mechanically ventilated target individual;
   at least one esophageal body having a pressure dependent volume, coupled to a distal portion of the feeding tube;
   a pressure sensor that senses the pressure on the at least one esophageal body while the feeding tube is in use;
   at least one hardware processor executing a code for:
   in a plurality of iterations synchronized with operation of a mechanical ventilator, ventilating the target individual:
      in a first inflation stage before the mechanical ventilator pushes air into lungs of the target individual:
         inflating the at least one esophageal body for contacting the esophageal wall for balancing alveoli pressure applied by the lungs;
         sensing a first pressure of the at least one esophageal body;
      in a second inflation stage after the mechanical ventilator pushed air into the lungs and after at least one of a selected volume is inserted to the at least one esophageal body and a selected pressure is reached within the the at least one esophageal body and before the mechanical ventilator extracted air from the lungs:
         sensing a second pressure of the at least one esophageal body; and
         computing the transpulmonary pressure of the mechanically ventilated target individual based on the second pressure and the first pressure.

2. The system according to claim 1, further comprising code instructions for detecting a gastric reflux event based on an analysis of at least one impedance value measured by at least one impedance sensor located on a distal end of the feeding tube, and code for generating instructions for inflating the at least one esophageal body in response to the detected gastric reflux event.

3. The system according to claim 1, further comprising code instructions for sensing an estimated amount of lung fluid in at least one lung of the target individual based on an analysis of at least one impedance value measured by at least one impedance sensor located on a distal end of the feeding tube, and code for generating instructions for periodically inflating the at least one esophageal body for periodic monitoring of the amount of lung fluid.

4. The system according to claim 1, further comprising:
   code for computing a trend curve according to a plurality of esophageal wall pressures measured over a plurality of ventilation cycles for each periodic inflation of the at least one esophageal body, wherein each ventilation cycle mechanically performs inhalation and exhalation for the target individual; and
   wherein the transpulmonary pressure is estimated according to the trend curve.

5. The system according to claim 1, further comprising:
   code for computing a trend curve according to a plurality of transpulmonary pressures measured over a historical time interval; and
   code for predicting a future transpulmonary pressure at a future time interval according to the trend curve.

6. The system according to claim 5, further comprising:
   code for generating an alert for presentation on a display of a client terminal when the future transpulmonary pressure at the future time interval is predicted to increase above a threshold transpulmonary pressure.

7. The system according to claim 6, wherein the threshold is indicative of onset of acute respiratory distress syndrome (ARDS).

8. The system according to claim 1, further comprising code for computing an estimate of a value of a Young modulus indicative of lung wall elasticity according to the computed transpulmonary pressure.

9. The system according to claim 1, further comprising code for inflating the at least one esophageal body to according to a predefined volume.

10. The system according to claim 1, wherein the feeding tube includes an enteral feeding tube having a distal end designed for positioning within the digestive system when in use for enteral feeding.

11. The system according to claim 1, wherein the feeding tube includes a nasogastric tube having a distal end designed for positioning within the digestive system when in use.

12. The system according to claim 1, wherein the feeding is sized and shaped for being disposed within the esophagus so that at least a distal end thereof is in the stomach lumen of the target individual while at least one segment including the at least one esophageal body is placed in the esophagus of the target individual.

13. The system according to claim 1, wherein the at least one esophageal body is located within about 0-5 centimeters from the lower esophageal sphincter (LES) when inflated and contacting the inner wall of the esophagus.

14. The system according to claim 1, further comprising code for computing a work of breathing (WOB) according to the computed transpulmonary pressure.

15. The system according to claim 14, further comprising code for presenting within a GUI, a pressure-volume graph depicting the WOB computed for the target individual and a reference WOB curve estimated for normal functioning lungs.

16. The system according to claim 14, further comprising code for presenting within a GUI, a trend curve indicative of a plurality of WOB values measured over a historical period of time.

17. The system according to claim 14, further comprising code for predicting a future WOB value at a future time interval based on an analysis of a plurality of historical computed WOB values.

18. The system according to claim 1, further comprising code for computing instructions for adjustment of at least one parameter of a mechanical ventilator that automatically mechanically ventilates the target individual according to the predicted future WOB value, wherein the instructions are transmitted to the mechanical ventilator over a network,
wherein the instructions for adjustment of at least one parameter of the mechanical ventilator are computed while the feeding tube is in place without removal of the feeding tube.

19. The system according to claim 1, wherein computing the transpulmonary pressure of the mechanically ventilated target individual comprises computing a difference between the second pressure and the first pressure.

20. The system according to claim 19, further comprising monitoring for development of ARDS by monitoring over the plurality of iterations, the difference between the second pressure and the first pressure relative to a threshold indicative of development of ARDS.

21. The system according to claim 1, further comprising, in the second inflation stage: injecting an additional volume into the at least one esophageal body, wherein the sensing the second pressure is performed after the injecting.

22. A method of monitoring a transpulmonary pressure of a mechanically ventilated target individual, the method comprising:

providing a feeding tube for insertion into a distal end of an esophagus of the mechanically ventilated target individual, wherein at least one esophageal body having a pressure dependent volume is coupled to a distal portion of the feeding tube;

in a plurality of iterations synchronized with operation of a mechanical ventilator ventilating the target individual:

in a first inflation stage, before the mechanical ventilator pushes air into lungs of the target individual, inflating the at least one esophageal body for contacting the esophageal wall for balancing alveoli pressure applied by the lungs;

sensing a first pressure of the at least one esophageal body;

in a second inflation stage, after the mechanical ventilator pushed air into the lungs and before the mechanical ventilator extracted air from the lungs and after at least one of a selected volume is inserted to the at least one esophageal body and a selected pressure is reached within the at least one esophageal body, sensing a second pressure of the at least one esophageal body;

computing the transpulmonary pressure of the mechanically ventilated target individual based on the second pressure and the first pressure.

* * * * *